US011727282B2

(12) United States Patent
Feinberg et al.

(10) Patent No.: US 11,727,282 B2
(45) Date of Patent: Aug. 15, 2023

(54) SYSTEMS AND METHODS FOR SPATIAL GRAPH CONVOLUTIONS WITH APPLICATIONS TO DRUG DISCOVERY AND MOLECULAR SIMULATION

(71) Applicant: The Board of Trustees of the Leland Stanford Junior University, Stanford, CA (US)

(72) Inventors: Evan Nathaniel Feinberg, Palo Alto, CA (US); Vijay Satyanand Pande, Woodside, CA (US); Bharath Ramsundar, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 742 days.

(21) Appl. No.: 16/293,586

(22) Filed: Mar. 5, 2019

(65) Prior Publication Data
US 2019/0272468 A1    Sep. 5, 2019

Related U.S. Application Data

(60) Provisional application No. 62/638,803, filed on Mar. 5, 2018.

(51) Int. Cl.
*G06N 3/08* (2023.01)
*G16C 20/30* (2019.01)
(Continued)

(52) U.S. Cl.
CPC ............... *G06N 3/126* (2013.01); *G06N 3/02* (2013.01); *G06N 3/08* (2013.01); *G16B 15/30* (2019.02);
(Continued)

(58) Field of Classification Search
CPC ........ G06N 3/08; G06N 3/0481; G06N 3/084; G06N 3/126; G06N 3/0445; G06N 3/0454;
(Continued)

(56) References Cited

U.S. PATENT DOCUMENTS 6,128,606 A    10/2000    Bengio et al.
8,874,432 B2 *    10/2014    Qi .......................... G06F 40/30
                                                                704/9
(Continued)

FOREIGN PATENT DOCUMENTS

CN    104936982 A    9/2015
CN    107729717 A    2/2018
(Continued)

OTHER PUBLICATIONS

Kearnes et al. Molecular Graph Convolutions: Moving Beyond Fingerprints (Aug. 24, 2016) (Year: 2016).*
(Continued)

*Primary Examiner* — Ann J Lo
*Assistant Examiner* — Leonard A Sieger
(74) *Attorney, Agent, or Firm* — KPPB LLP

(57) ABSTRACT

Systems and methods for spatial graph convolutions in accordance with embodiments of the invention are illustrated. One embodiment includes a method for predicting characteristics for molecules, wherein the method includes performing a first set of graph convolutions with a spatial graph representation of a set of molecules, wherein the first set of graph convolutions are based on bonds between the set of molecules, performing a second set of graph convolutions with the spatial graph representation, wherein the second set of graph convolutions are based on at least a distance between each atom and other atoms of the set of molecules, performing a graph gather with the spatial graph represen-
(Continued)

tation to produce a feature vector, and predicting a set of one or more characteristics for the set of molecules based on the feature vector.

20 Claims, 8 Drawing Sheets

(51) Int. Cl.
    G16C 20/70    (2019.01)
    G06N 3/02    (2006.01)
    G16B 15/30    (2019.01)
    G16C 10/00    (2019.01)
    G16C 20/50    (2019.01)
    G06N 3/126    (2023.01)

(52) U.S. Cl.
    CPC ............. *G16C 20/30* (2019.02); *G16C 20/70* (2019.02); *G16C 10/00* (2019.02); *G16C 20/50* (2019.02)

(58) Field of Classification Search
    CPC .......... G06N 3/02; G16C 20/30; G16C 20/50; G16C 20/70; G16C 10/00; G16C 20/10; G16B 15/30; G16B 15/20; C07K 2/00
    See application file for complete search history.

(56) References Cited

U.S. PATENT DOCUMENTS

| | | | |
|---|---|---|---|
| 9,373,059 | B1 | 6/2016 | Heifets et al. |
| 10,923,214 | B2* | 2/2021 | Fan ..................... G16C 20/70 |
| 11,205,113 | B2* | 12/2021 | Riley .................... G16C 20/70 |
| 2002/0072587 | A1 | 6/2002 | Somers et al. |
| 2002/0099506 | A1* | 7/2002 | Floriano ................ G16B 15/30 703/11 |
| 2003/0215877 | A1 | 11/2003 | Love et al. |
| 2004/0248801 | A1 | 12/2004 | Kiessling et al. |
| 2005/0055187 | A1 | 3/2005 | Sherman et al. |
| 2007/0134662 | A1 | 6/2007 | Singh et al. |
| 2007/0196869 | A1 | 8/2007 | Perez et al. |
| 2009/0037136 | A1 | 2/2009 | Young et al. |
| 2015/0134315 | A1 | 5/2015 | Sarmiento et al. |
| 2015/0178442 | A1 | 6/2015 | Abel et al. |
| 2015/0193575 | A1 | 7/2015 | Houghton et al. |
| 2015/0355200 | A1 | 12/2015 | Ring et al. |
| 2016/0300127 | A1 | 10/2016 | Heifets et al. |
| 2017/0061276 | A1* | 3/2017 | Riley ..................... G16C 20/70 |
| 2018/0141958 | A1 | 5/2018 | Morikis et al. |
| 2018/0341754 | A1* | 11/2018 | Fan ..................... G06N 5/046 |
| 2019/0050538 | A1 | 2/2019 | Luo et al. |
| 2019/0139622 | A1* | 5/2019 | Osthege ................. G06N 3/084 |
| 2019/0272887 | A1 | 9/2019 | Feinberg et al. |
| 2019/0354689 | A1 | 11/2019 | Li et al. |

FOREIGN PATENT DOCUMENTS

| | | |
|---|---|---|
| CN | 112204402 A | 1/2021 |
| EP | 3762730 | 1/2021 |
| HK | 40038934 A | 7/2021 |
| HK | 40039264 A | 7/2021 |
| JP | 2005517630 A | 6/2005 |
| JP | 2016166159 A | 9/2016 |
| JP | 2021515233 A | 6/2021 |
| KR | 10-2020-0128710 A | 11/2020 |
| WO | 2002101077 A2 | 12/2002 |
| WO | 2015081166 A1 | 6/2015 |
| WO | 2017070160 A1 | 4/2017 |
| WO | 2017070718 A1 | 4/2017 |
| WO | 2017192872 A1 | 11/2017 |
| WO | 2019099573 A1 | 5/2019 |
| WO | 2019173401 A1 | 9/2019 |
| WO | 2019173407 A1 | 9/2019 |

OTHER PUBLICATIONS

Li et al. Learning Graph While Training: An Evolving Graph Convolutional Neural Network (Aug. 10, 2017) (Year: 2017).*
Merkwirth et al. Automatic Generation of Complementary Descriptors with Molecular Graph Networks (2005) (Year: 2005).*
Weiner et al. AMBER: Assisted Model Building with Energy Refinement. A General Program for Modeling Molecules and Their Interactions (Jan. 14, 1981) (Year: 1981).*
Li et al. Learning Graph-Level Representation for Drug Discovery (Sep. 16, 2017) (Year: 2017).*
Kearnes et al. Molecular Graph Convolutions: Moving Beyond Fingerprints (Aug. 24, 2016) Retrieved from the Internet <URL: https://link.springer.com/content/pdf/10.1007/s10822-016-9938-8.pdf > (Year: 2016).*
Li et al. Learning Graph While Training: An Evolving Graph Convolutional Neural Network (Aug. 10, 2017) Retrieved from the Internet <URL: https://arxiv.org/pdf/1708.04675.pdf > (Year: 2017).*
Merkwirth et al. Automatic Generation of Complementary Descriptors with Molecular Graph Networks (2005) Retrieved from the Internet <URL: https://pubs.acs.org/doi/pdf/10.1021/ci049613b > (Year: 2006).*
Zeiler et al., Stochastic Pooling for Regularization of Deep Convolutional Neural Networks (Jan. 16, 2013) Retrieved from the Internet <URL: https://arxiv.org/pdf/1301.3557.pdf > (Year: 2013).*
Gilmer et al., Neural Message Passing for Quantum Chemistry (2017) Retrieved from the Internet <URL: http://proceedings.mlr.press/v70/gilmer17a/gilmer17a.pdf > (Year: 2017).*
Such et al., Robust Spatial Filtering with Graph Convolutional Neural Networks (Jul. 14, 2017) Retrieved from the Internet <URL: https://arxiv.org/pdf/1703.00792.pdf > (Year: 2017).*
Rumelhart et al., Learning representations by back-propagating errors (1986) Retrieved from the Internet <URL: http://www.cs.utoronto.ca/~hinton/absps/naturebp.pdf > (Year: 1986).*
Weiner et al. AMBER: Assisted Model Building with Energy Refinement. A General Program for Modeling Molecules and Their Interactions (Jan. 14, 1981) Retrieved from the Internet <URL: https://onlinelibrary.wiley.com/doi/epdf/10.1002/jcc.540020311 > (Year: 1981).*
Cang et al., "TopologyNet: Topology based deep convolutional and multi-task neural networks for biomolecular property predictions", 2017, PLoS Computational Biology, vol. 13(7), pp. 1-27 (Year: 2017).*
Ballester et al., "Does a more precise chemical description of protein-ligand complexes lead to more accurate prediction of binding affinity?", 2014, Journal of chemical information and modeling, vol. 54(3), pp. 944-955 (Year: 2017).*
Kearnes et al., "Molecular Graph Convolutions: Moving Beyond Fingerprints", 2016, arXiv, v1603.00856v3, pp. 1-29 (Year: 2016).*
Faber et al., "Prediction Errors of Molecular Machine Learning Models Lower than Hybrid DFT Error", 2017, Journal of Chemical Theory and Computation, vol. 13 (11), pp. 5255-5264 (Year: 2017).*
Heck et al., "Supervised Machine Learning Methods Applied to Predict Ligand Binding Affinity", 2017, Current Medicinal Chemistry, vol. 24, pp. 2459-2470 (Year: 2017).*
Artemenko, Natalia, "Distance dependent scoring function for describing protein-ligand intermolecular interactions", 2008, Journal of Chemical Information and Modeling, vol. 48(3), pp. 569-574. (Year: 2008).*
Ballester et al., "Does a more precise chemical description of protein-ligand complexes lead to more accurate prediction of binding affinity?", 2014, Journal of chemical information and modeling, vol. 54(3), pp. 944-955 (Year: 2014).*
Keil et al., "Pattern recognition strategies for molecular surfaces: III. Binding site prediction with a neural network", 2004, Journal of Computational Chemistry, vol. 25(6), pp. 779-789 (Year: 2004).*
Gang et al., "TopologyNet: Topology based deep convolutional and multi-task neural networks for biomolecular property predictions", 2017, PLoS Computational Biology, vol. 13(7), pp. 1-27 (Year: 2017).*

(56) References Cited

OTHER PUBLICATIONS

Fout et al., "Protein Interface Prediction using Graph Convolutional Networks", 2017, 31stConference on Neural Information Processing Systems, vol. 31 (2017), pp. 1-10 (Year: 2017).*
Xu et al., "An overview of neural networks for drug discovery and the inputs used", 2018, Expert Opinion on Drug Discovery, vol. 13 (12) (2018), pp. 1091-1102 (Year: 2018).*
Pereira et al., "Boosting Docking-based Virtual Screening with Deep Learning", 2016, arXiv, v1608.04844v2, pp. 1-18 (Year:2016).*
Ain et al., "Machine-learning scoring functions to improve structure-based binding affinity prediction and virtual screening", 2015, Comput Mol Sci, vol. 5 (2017): pp. 405-424. (Year: 2017).*
Ashtawy, "Data-Driven and Task-Specific Scoring Functions for Predicting Ligand Binding Poses and Affinity and for Screening Enrichment", 2017, Dissertation Submitted to Michigan State University (Year: 2017).*
Ballester et al., "A machine learning approach to predicting protein—ligand binding affinity with applications to molecular docking", 2010, Bioinformatics, vol. 26 No. 9, pp. 1169-1175 (Year: 2010).*
Bortolato et al., "Molecular Docking Methodologies", 2012, Methods in Molecular Biology, vol. 924 pp. 339-360 (Year: 2012).*
Hayatshahi, "The Effect of Atomistic Interactions on Rna Conformational Distributions, Folding and Ligand Binding Via Molecular Dynamics Simulations and Docking", 2017, Dissertation Submitted to The University of Utah (Year: 2017).*
Martiny et al., "In Silico Mechanistic Profiling to Probe Small Molecule Binding to Sulfotransferases", 2016, PLoS One, vol. 8 (2013), pp. 1-13 (Year: 2013).*
International Search Report and Written Opinion for International Application No. PCT/US2019/020843, completed May 2, 2019, dated May 17, 2019, 13 pgs.
International Search Report and Written Opinion for International Application No. PCT/US2019/020837, completed Jun. 10, 2019, dated Jul. 10, 2019, 14 pgs.
Invitation to Pay Add'l Fees and Partial Search Rpt Rcvd for International Application PCT/US2019/020837, Mailed May 2, 2019, 3 pgs.
Coley et al., "Convolutional Embedding of Attributed Molecular Graphs for Physical Property Prediction", Journal of Chemical Information and Modeling, 2007, vol. 57, No. 8, pp. 1757-1772, http://dx.doi.org/10.1021/acs.jcim.6b00601.
Doerr et al., S., "Dimensionality reduction methods for molecular simulations", arXiv preprint arXiv: 1710.10629, Oct. 29, 2017, pp. 1-11.
Feinberg, Evan N. et al., "Machine Learning Harnesses Molecular Dynamics to Discover New μ Opioid Chemotypes", ArXiv preprint arXiv:1803.04479, Mar. 12, 2018, 6 pgs.
Feinberg, Evan N., "Molecular Dynamics with Spatial Graph Convolutions", A Whitepaper and Project Proposal, Program in Biophysics, Stanford University, pp. 1-6.
Feinberg et al., Evan N., "Spatial Graph Convolutions for Drug Discovery", ArXiv preprint arXiv:1803.04465, 2018, pp. 1-15.
Feinberg et al., "PotentialNet for Molecular Property Prediction", ACS Central Science, Nov. 2, 2018, vol. 4, pp. 1520-1530.
Gilmer et al., "Neural Message Passing for Quantum Chemistry", Proceedings of the 34th International Conference on Machine Learning, Sydney, Australia, PMLR 70, 2017, 14 pgs., arXiv:1704.01212, Jun. 12, 2017.
Gomes et al., "Atomic Convolutional Networks for Predicting Protein-Ligand Binding Affinity", Mar. 30, 2017; Abstract; p. 2, para. 3; Figures 1, 2 Tables 1-4; and entire document, pp. 1-17, arXiv:1703.10603.
Hochuli et al., "Visualizing Convolutional Neural Network Protein-Ligand Scoring", Journal of Molecular Graphics and Modeling (preprint), Mar. 8, 2018, pp. 1-11, arXiv:1803.02398, Mar. 6, 2018.
Kearnes et al., "Molecular graph convolutions: moving beyond fingerprints", J. Comp. Aided Mol. Des., 2016, vol. 30, No. 8; pp. 595-608, Author manuscript; available in PMC Aug. 24, 2017, doi:10.1007/s10822-016-9938-8.
Kitchen et al., "Docking and scoring in virtual screening for drug discovery: methods and applications", Nature Reviews | Drug Discovery, Nov. 2004, vol. 3, pp. 935-949.
Li et al., "Gated Graph Sequence Neural Networks", arXiv preprint arXiv:1511.05493, 2015, pp. 1-20.
Mcgibbon, Robert T., The Journal of Chemical Physics, vol. 146, No. 4, 2017, 18 pgs., arXiv:1602.08776, Jan. 6, 2017.
Wu et al., "MoleculeNet: a benchmark for molecular machine learning", Chemical Science, 2018, vol. 9, pp. 513-530.
Zhou, Zhenpeng, "Convolution on Graph: A High-Order and Adaptive Approach", arXiv:1706.09916 (Oct. 20, 2017), 2018, 8 pgs.
Extended European Search Report for European Application No. 19763344.9, Search completed Oct. 22, 2021, dated Nov. 2, 2021, 12 Pgs.
Extended European Search Report for European Application No. 19764602.9, Search completed Oct. 22, 2021, dated Nov. 2, 2021, 8 Pgs.
International Preliminary Report on Patentability for International Application PCT/US2019/020837, Report dated Sep. 8, 2020, dated Sep. 17, 2020, 10 Pgs.
International Preliminary Report on Patentability for International Application PCT/US2019/020843, Report dated Sep. 8, 2020, dated Sep. 17, 2020, 5 Pgs.
Ballester, "Machine Learning Scoring Functions Based on Random Forest and Support Vector Regression," International Conference on Imae Analysis and Processing, 17th International Conference, Nov. 8, 2012, XP047470176, 12 pgs.
Feinberg et al., "Kinetic Machine Learning Unravels Ligand-Directed Conformational Change of μ Opioid Receptor," BioRxiv, Jul. 31, 2017, XP055853266. 18 Pgs.
Li et al., "Adaptive Graph Convolutional Neural Networks", arxiv.org, Cornell University Library, Jan. 10, 2018, XP081205326.
Shang et al., "Edge Attention-Based Multi-Relational Graph Convolutional Networks," arxiv.org, Cornell University Library, Feb. 14, 2018, XP080856627.
Coleman et al., "Ligand Pose and Orientational Sampling in Molecular Docking", PLOS One, 2013, vol. 8, Issue 10.
Li et al., "Prediction of Estrogen Receptor Agonists and Characterization of Associated Molecular Descriptors by Statistical Learning Methods", Journal of Molecular Graphics and Modelling, 2006, vol. 25, pp. 313-323.
Mitchell, "Machine Learning Methods in Chemoinformatics", The Authors, WIREs Computational Molecular Science, Sep./Oct. 2014, vol. 4, 14 pgs.
Zilian et al., "SFCscoreRF: A Random Forest-Based Scoring Function for Improved Affinity Prediction of Protein-Ligand Complexes", Journal of Chemical Information and Modeling, 2013, vol. 53, pp. 1923-1933.
Krumm et al., "Structure and Dynamics of a Constitutively Active Neurotensin Receptor", Scientific Reports, 2016 | 6:38564.
Niesen et al., "The Role of Conformational Ensembles in Ligand Recognition in G-Protein Coupled Receptors", J. Am. Chem. Soc. 2011, 133, 13197-13204.
Shukla et al., "Elucidating Ligand-Modulated Conformational Landscape of GPCRs Using Cloud-Computing Approaches", Methods in Enzymology, 2014, vol. 557.
English Translation of Office for Japanese Patent Application No. 2020-546374, dated Apr. 3, 2023, 7 pages.
Ain et al., "Machine-learning scoring functions to improve structure-based binding affinity prediction and virtual screening", Comput Mol Sci 2015, 5:405-424.
Ashtawy, "Data-Driven and Task-Specific Scoring Functions for Predicting Ligand Binding Poses and Affinity and for Screening Enrichment", Dissertation Submitted to Michigan State University (Year: 2017).
Ballester et al., "A machine learning approach to predicting protein—ligand binding affinity with applications to molecular docking", Advance Access publication Mar. 17, 2010, vol. 26, No. 9, pp. 1169-1175.
Bortolato et al., "Molecular Docking Methodologies", Biomolecular Simulations. Methods in Molecular Biology, vol. 924, pp. 339-360 (2012).

(56) References Cited

OTHER PUBLICATIONS

Hayatshahi, "The Effect of Atomistic Interactions on Rna Conformational Distributions, Folding and Ligand Binding Via Molecular Dynamics Simulations and Docking", The University of Utah, 2017.

Martiny et al., "In Silico Mechanistic Profiling to Probe Small Molecule Binding to Sulfotransferases", PLoS One, 2013, vol. 8, e73587.

* cited by examiner

SYSTEMS AND METHODS FOR SPATIAL GRAPH CONVOLUTIONS WITH APPLICATIONS TO DRUG DISCOVERY AND MOLECULAR SIMULATION

CROSS-REFERENCE TO RELATED APPLICATIONS

The present application claims the benefit of and priority to U.S. Provisional Patent Application No. 62/638,803 entitled "Spatial Graph Convolutions with Applications to Drug Discovery", filed Mar. 5, 2018. The disclosure of U.S. Provisional Patent Application Ser. No. 62/638,803 is herein incorporated by reference in its entirety.

STATEMENT OF FEDERALLY-SPONSORED RESEARCH

This invention was made with government support under Grant No. AI109662 awarded by the National Institutes of Health. The government has certain rights in the invention.

FIELD OF THE INVENTION

The present invention generally relates to predicting molecular characteristics and more specifically relates to utilizing spatial graph convolutions to predict molecular characteristics.

BACKGROUND

Most FDA-approved drugs are small organic molecules that elicit a therapeutic response by binding to a target biological macromolecule. Once bound, small molecule ligands either inhibit the binding of other ligands or allosterically adjust the target's conformational ensemble. Binding is thus crucial to any behavior of a therapeutic ligand. To maximize a molecule's therapeutic effect, its affinity—or binding free energy ($\Delta G$)—for the desired targets must be maximized, while simultaneously minimizing its affinity for other macromolecules. Historically, scientists have used both cheminformatic and structure-based approaches to model ligands and their targets, and most machine learning (ML) approaches use domain expertise-driven features.

SUMMARY OF THE INVENTION

Systems and methods for spatial graph convolutions in accordance with embodiments of the invention are illustrated. One embodiment includes a method for predicting characteristics for molecules, wherein the method includes performing a first set of graph convolutions with a spatial graph representation of a set of molecules, wherein the first set of graph convolutions are based on bonds between the set of molecules, performing a second set of graph convolutions with the spatial graph representation, wherein the second set of graph convolutions are based on at least a distance between each atom and other atoms of the set of molecules, performing a graph gather with the spatial graph representation to produce a feature vector, and predicting a set of one or more characteristics for the set of molecules based on the feature vector.

In a further embodiment, the method further includes steps for receiving atomic information for the set of one or more molecules.

In still another embodiment, the method further includes steps for building a spatial graph representation of the set of molecules.

In a still further embodiment, building the spatial graph representation includes generating a distance matrix and an adjacency tensor, wherein the distance matrix denotes distances between atoms of the set of molecules and the adjacency tensor indicates multiple different edge types between atoms.

In yet another embodiment, the set of molecules includes a ligand molecule and a target molecule, wherein rows of the distance matrix are ordered by membership in the ligand and target molecules.

In a yet further embodiment, the bonds between the set of molecules includes covalent bonds.

In another additional embodiment, the bonds between the set of molecules includes at least one of $\pi$-$\pi$ stacking, hydrogen bonds, and hydrophobic contact.

In a further additional embodiment, the second set of graph convolutions are further based on bonds between the set of molecules.

In another embodiment again, the first set of graph convolutions is based on a first set of the bonds between the set of molecules and the second set of graph convolutions is based on a second set of the bonds between the set of molecules.

In a further embodiment again, the first set of bonds is a subset of the second set of bonds.

In still yet another embodiment, performing the first set of graph convolutions includes performing a gated recurrent unit (GRU) operation at each layer of the graph convolutions.

In a still yet further embodiment, performing the first set of graph convolutions includes utilizing a first plurality of neural networks, wherein each neural network of the plurality of neural networks is used for a different bond type.

In still another additional embodiment, performing the second set of graph convolutions includes utilizing a second plurality of neural networks, wherein weights for the first plurality of neural networks are shared with the second plurality of neural networks.

In a still further additional embodiment, performing the second set of graph convolutions includes utilizing a second plurality of neural networks, wherein the neural networks of the second plurality of neural networks utilize distance information regarding distances between atoms of the set of molecules.

In still another embodiment again, the set of molecules includes a ligand molecule and a target molecule, wherein the graph gather is performed solely on the ligand molecule.

In a still further embodiment again, the set of characteristics includes whether a first molecule of the set of molecules binds with a second molecule of the set of molecules.

Systems and methods for training spatial convolution graph models in accordance with embodiments of the invention are illustrated. One embodiment includes a method for training a spatial convolution graph model. The method includes steps for performing a first set of graph convolutions with a spatial convolution graph model of a set of molecules, wherein the first set of graph convolutions are based on bonds between the set of molecules, performing a second set of graph convolutions with the spatial convolution graph model, wherein the second set of graph convolutions are based on at least a distance between each atom and other atoms of the set of molecules, performing a graph gather with the spatial convolution graph model, computing loss for the set of molecules based on the graph gather, and updating the spatial convolution graph model based on the computed loss.

In yet another additional embodiment, the method further includes steps for using layers of the spatial convolution graph model to train a set of one or more neural networks to predict a set of one or more parameters for a force field.

In a yet further additional embodiment, the set of parameters is associated with a set of one or more characteristics, wherein the set of characteristics include at least one of charges, bonds, angles, and dihedrals.

In yet another embodiment again, the spatial convolution graph model is a first spatial convolution graph model, wherein the method further includes training a second spatial convolution graph model to predict potential energy, and predicting a potential energy of a molecular system based on the first and second spatial convolution graph models.

In a yet further embodiment again, training the second spatial convolution graph model includes sharing a set of one or more layers between the first and second spatial convolution graph models.

In another additional embodiment again, the force field is an Assisted Model Building with Energy Refinement (AMBER) functional form.

In a further additional embodiment again, the method further includes steps for using layers of the spatial convolution graph model to train a set of one or more neural networks to predict a potential energy of an input molecular system.

In still yet another additional embodiment, the method further includes steps for identifying a set of conformations of the set of molecules by minimizing the potential energy predicted by the spatial graph convolution model.

In a further embodiment, the method further includes steps for predicting motion of the set of molecules.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
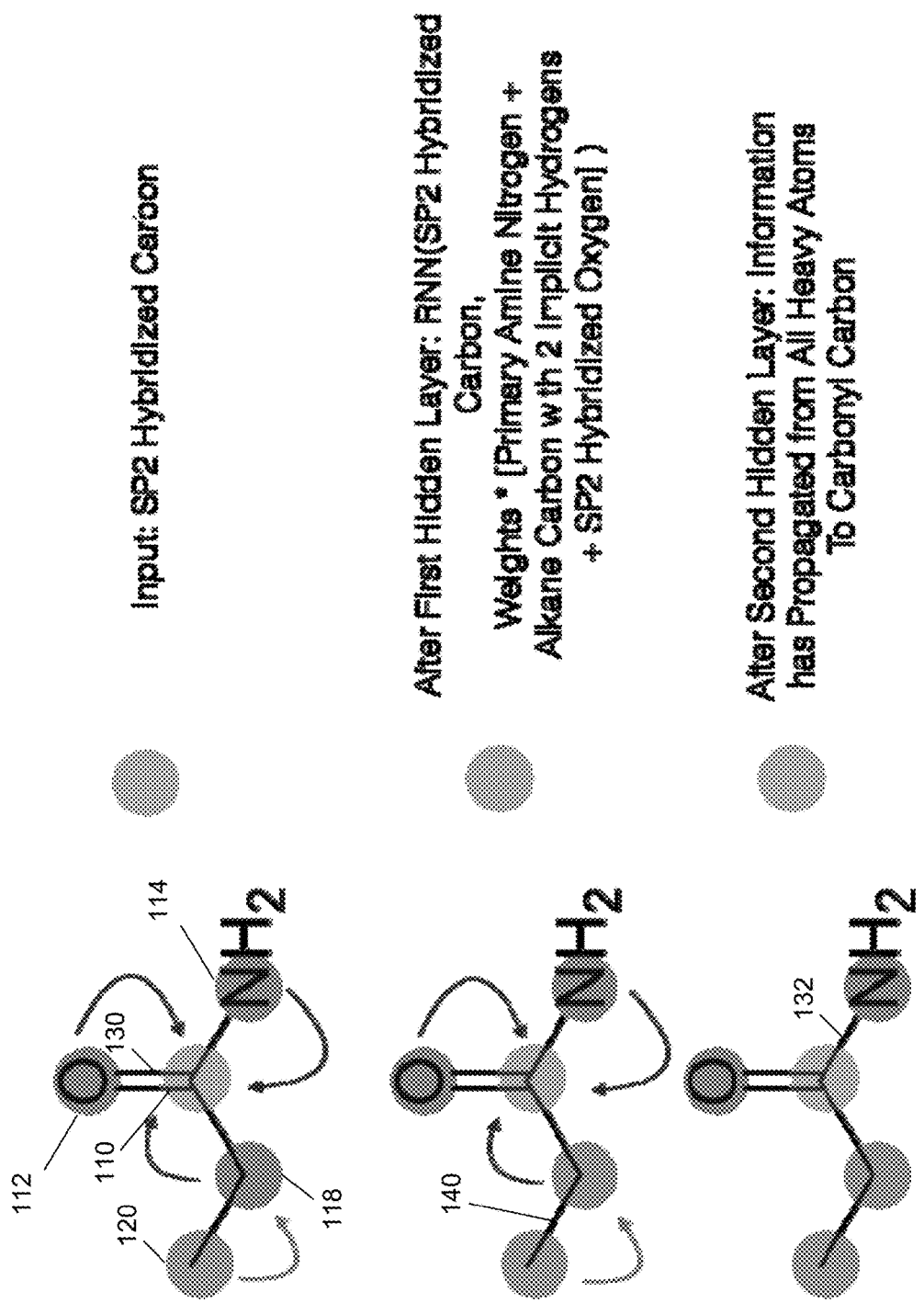
FIG. 1 illustrates a visual depiction of a Gated Graph Neural Network (GGNN).

Systems and methods in accordance with numerous embodiments of the invention are specifically designed for and achieve state-of-the-art performance for protein-ligand binding affinity. Although many of the examples in this application are described with reference to binding affinities, many molecular characteristics such as, but not limited to, toxicity, solubility, and electronic properties can be predicted without departing from the spirit of the invention. In many embodiments, processes utilize a multi-stage process based on bond types and spatial distances to predict molecular characteristics. In some embodiments, a new metric, the Regression Enrichment Factor $EFx^)$, is computed to measure the early enrichment of computational models for chemical data. Processes in accordance with a variety of embodiments of the invention implement a cross-validation strategy based on structural homology clustering that can more accurately measure model generalizability, which crucially distinguishes the aims of machine learning for drug discovery from standard machine learning tasks.

The arc of drug discovery entails a multiparameter optimization problem spanning vast length scales. The key parameters range from solubility (angstroms) to protein-ligand binding (nanometers) to in vivo toxicity (meters). Historically, scientists have used both cheminformatic and structure-based approaches to model ligands and their targets, and most machine learning (ML) approaches use domain expertise-driven features. Through feature learning-instead of feature engineering-deep neural networks promise to outperform both traditional physics-based and knowledge-based machine learning models for predicting molecular properties pertinent to drug discovery.

Training most conventional DNN architectures requires vast amounts of data: for example. ImageNet currently contains over 14,000,000 labeled images. In contrast, the largest publicly available datasets for the properties of drug-like molecules include PDBBind 2017, with a little over 4,000 samples of protein-ligand co-crystal structures and associated binding affinity values; Tox21 with nearly 10,000 small molecules and associated toxicity endpoints; QM8 with around 22,000 small molecules and associated electronic properties; and ESOL with a little over 1,000 small molecules and associated solubility values. This scarcity of high-quality scientific data necessitates innovative neural architectures for molecular machine learning.

Successful DNNs often exploit relevant structure in data, such as pixel proximity in images. Predicting protein-ligand binding affinity can be seen as similar to computer vision problems. Just as neighboring pixels connote closeness between physical objects, a binding pocket could be divided into a voxel grid. Here, neighboring voxels denote neighboring atoms and blocks of empty space. Unfortunately, this 3D convolutional approach has several potential drawbacks. First, inputs and hidden weights require much more memory in three dimensions. Second, since the parameters grow exponentially with the number of dimensions, the model suffers from the "curse of dimensionality". The qualitatively simplest models for affinity prediction and related tasks incorporate only features of ligands and ignore the macromolecular target(s).

A graph convolutional neural network (GCNN) analogously exploits the inherent structure of data. Graph convolutions can use fewer parameters by exploiting molecular structure and symmetry. Graph convolutions can be symmetric to permutations and to the relative location of each of the neighboring nodes, thereby significantly reducing the number of model parameters. Models in accordance with several embodiments of the invention can generalize a graph convolution to include both intramolecular interactions and noncovalent interactions between different molecules.

In several embodiments, processes can employ a staged gated graph neural network, which distinguishes the derivation of differentiable bonded atom types from the propagation of information between atoms through space. Processes in accordance with some embodiments of the invention employ a more flexible model based on a new update rule using both the distance from source to target atom and the target atom's feature map. Direct incorporation of target atom information into the message function can increase signal in some protein-ligand binding affinity benchmarks.

In several embodiments, a given graph that contains N nodes, $f_{in}$ features per node, and a single edge type, can be represented as consisting of node features x and symmetric adjacency matrix A, which designates whether a pair of nodes belong to each other's neighbor sets N. Turning now to the drawings, a visual depiction of a Gated Graph Neural Network (GGNN) is illustrated in FIG. 1. GGNN 100 is illustrated with nodes (110-120), representing atoms, and edges (130-140), representing bonds. In this example, the small molecule propanamide is chosen to illustrate the propagation of information among the different update layers of the network. For the carbonyl carbon (110), the relevant row of the feature matrix x might be [1,0,0] to represent its element, and the corresponding row of the adjacency matrix A might be [0, 1, 0, 1, 1] to indicate its bonds to three neighbor atoms.

In a number of embodiments, a graph convolution update entails applying a function at each node that takes the node and its neighbors as input and outputs a new set of features for each node. Graph convolutions are described in "Neural message passing for quantum chemistry" by Gilmer et al., Proceedings of the 34th International Conference on Machine Learning, the disclosure of which is incorporated by reference herein in its entirety. A graph convolution can be written as $$h_i^{(t+1)} = U^{(t)}\left(h_i^{(t)}, \sum_{v_j \in N(v_i)} m^{(t)}\left(h_j^{(t)}\right)\right), \quad (1)$$

where $h_i^{(t)}$ represents the node features of node i at hidden layer t, $N(v_i)$ represents the neighbors of node i, and $U^{(t)}$ and $m^{(t)}$ are the update and message functions, respectively, at hidden layer t. In certain embodiments, when there are multiple edge types, multiple message functions can be defined, $n^{(t,e)}$, which is the message function at layer t for edge type $e \in [1, \ldots, N_{et}]$.

In many embodiments, the update function at all layers of the model is the familiar gated recurrent unit (GRU). However, one skilled in the art will recognize that other update functions can be used without departing from the spirit of the invention. In some embodiments, message functions are simple linear operations that are different for each edge type but also the same across layers:

$$h_i^{(t+1)} = GRU\left(h_i^{(t)}, \sum_{e}^{N_{et}} W^{(e)} A^{(e)} h^{(t)}\right), \quad (2)$$

where $A^{(e)}$ is the adjacency matrix, and $W^{(e)}$ the weight matrix, respectively, for edge type e.

The GGNN family of graph convolutional architectures includes effective optimizations to reduce complexity on graphs. Let d be the dimension of each node's internal hidden representation and n be the number of nodes in the graph. A single step of message passing for a dense graph requires $\mathcal{O}(n^2 d^2)$ multiplications. Breaking the d dimensional node embeddings into k different $$\frac{d}{k}$$

dimensional embeddings reduces this runtime to $$\mathcal{O}\left(\frac{n^2 d^2}{k}\right).$$

As most molecules are sparse or relatively small graphs, these layers are typically $$\mathcal{O}\left(\frac{n d^2}{k}\right).$$

In a variety of embodiments, other optimizations can be employed, such as (but not limited to) utilizing spectral representations of graphs.

Unlike conventional FCNNs, which learn non-linear combinations of the input hand-crafted features, the update described in accordance with some embodiments of the invention learns nonlinear combinations of more basic features of a given atom with the features of its immediate neighbors. Information propagates through increasingly distant atoms with each graph convolution, and the GRU enables information to be added selectively. Ultimately, the GCNN contains and leverages both per-node features via the feature matrix x and structural information via the adjacency matrix A. In both classification and regression settings, GCNN's can terminate in a "graph gather" step that sums over the rows of the final embeddings and is invariant to node ordering. The subsequent FCNNs produce output of desired size ($f_{out}$). This completes the starting point for the graph convolution update used in accordance with many embodiments of the invention:

$$\blacksquare = GRU\left(x, \sum_{e}^{N_{et}} W^{(e)}A^{(e)}x\right) \qquad (3)$$

$$\vdots$$

$$h^{(k)} = GRU\left(h^{(K-1)}, \sum_{e}^{N_{et}} W^{(e)}A^{(e)}h^{(K-1)}\right)$$

$$h^{(FC_0)} = \sum_{r=1}^{N} [\sigma(i(h^{(K)}, x)) \odot (j(h^{(K)}))]_r$$

$$\in \mathbb{R}^{(1 \times f_{out})}$$

$$h^{(FC_1)} = ReLU\left(W^{(FC_1)} \cdot h^{(FC_0)}\right)$$

$$\vdots$$

$$h^{(FC_M)} = ReLU\left(W^{(FC_M)} \cdot h^{(FC_{M-1})}\right)$$

In certain embodiments, predicting affinity for multiple targets by GCNN can be implemented by training either different models for each target or by training a single multitask network. The latter setting in accordance with various embodiments of the invention can use a last weight matrix $$W^{(FC_M)} \in \mathbb{R}^{(T \times f_{FC_{M-1}})},$$

where T denotes the number of targets in the dataset. The corresponding multitask loss function would be the average binary cross-entropy loss across the targets, $$Loss_{multitask} = \frac{1}{T}\sum_{j}^{T}\left[\frac{1}{n_j}\sum_{i}^{n_j}(y_i \cdot \log(\sigma(\hat{y}_i))) + (1 - y_i) \cdot \log(1 - \sigma(\hat{y}_i)))\right] \qquad (4)$$

Systems and methods in accordance with numerous embodiments of the invention leverage structural information about the target in addition to the ligand. To motivate architectures for more principled DNN predictors, the following notation and framework is used. A distance matrix $R \in \mathbb{R}^{(N \times N)}$, whose entries $R_{ij}$ denote the distance between atom$_i$ and atom$_j$.

Thus far, the concept of adjacency, as encoded in a symmetric matrix A, has been restricted to chemical bonds. However, adjacency can also encompass a wider range of neighbor types to include non-covalent interactions (e.g., π-π stacking, hydrogen bonds, hydrophobic contact). Adjacency need not require domain expertise. In a variety of embodiments, pairwise distances below a threshold value can also be used. Regardless of particular scheme, the distance matrix R motivates the construction of an expanded version of A. In this framework, A becomes a tensor of shape $N \times N \times N_{et}$, where $N_{et}$ represents the number of edge types.

If the rows are ordered by the membership of atom$_i$ to either the protein or ligand, both A and R can be viewed as block matrices, where the diagonal blocks are self-edges (i.e., bonds and non-covalent interactions) from one ligand atom to another ligand atom or from one protein atom to another protein atom. Off-diagonal block matrices can encode edges from the protein to the ligand and from ligand to protein. For the purpose of simplicity, the special case where there is only one edge type. $N_{et}=1$ is described:

$$A = \begin{bmatrix} A_{11} & A_{12} & \cdots & A_{1N} \\ A_{21} & A_{22} & \cdots & A_{2N} \\ \vdots & \vdots & \ddots & \vdots \\ A_{N1} & A_{N2} & \cdots & A_{NN} \end{bmatrix} = \begin{bmatrix} A_{L:L} & A_{L:P} \\ A_{P:L} & A_{P:P} \end{bmatrix}, \qquad (5)$$

where $A_{ij}$ is 1 for neighbors and 0 otherwise, and $A \in \mathbb{R}^{N \times N}$. Within this framework, a spatial graph convolution—a graph convolution based on notions of adjacency predicated on Euclidean distance—can be expressed as a generalization of the GGNN characterized by the update described above.

In addition to edge type generalization, processes in accordance with many embodiments of the invention introduce nonlinearity in the message portion of the graph convolutional layer:

$$h_i^{(K)} = GRU\left(h_i^{(K-1)}, \sum_{e}^{N_{et}} \sum_{j \in N^{(e)}(v_i)} NN^{(e)}(h_j^{(K-1)})\right), \qquad (6)$$

where $NN^{(e)}$ is a neural network for each edge type e and $N^{(e)}(h_i)$ denotes the neighbors of edge type e for atom/node i.

In several embodiments, the concept of a layer is generalized to the notion of a stage that can span several layers of a given type. Processes in accordance with some embodiments of the invention consist of three main steps: (1) covalent-only propagation. (2) dual non-covalent and covalent propagation, and (3) ligand-based graph gather. More generally, in some embodiments, processes perform a first propagation based on a first set of one or more edge types. The second stage in accordance with a variety of embodiments of the invention can include the bond types as well as distance information, separate from bond information, from a distance matrix. Distance information can include (but is not limited to) specific physical distance measurements and/or binned distances. The second stage in accordance with various embodiments of the invention can include all of the edge types or a subset of the edge types.

In certain embodiments, stage (1), covalent propagation, entails only the first slice of the adjacency matrix, $A^{(1)}$, which contains a 1 at entry (i, j) if there is a bond between (atom$_i$,atom$_j$) and a 0 otherwise. Intuitively, stage (1) computes a new set of vector-valued atom types $h_i^{(1)}$ for each of the N atoms in the system based on their local networks of bonded atoms. Atom types in accordance with various embodiments of the invention are feature maps for each atom. Subsequently, stage (2) in accordance with a variety of embodiments of the invention entails propagation based on both the full adjacency tensor A which begins with the vector-valued atom types $h_i^{(1)}$ computed in (1). While stage (1) computes new bond-based "atom types" for both amino acid and ligand atoms, stage (2) passes both bond and spatial information between the atoms. For instance, if stage (1) distinguishes an amide carbonyl oxygen from a ketone carbonyl oxygen, stage (2) might communicate in the first layer that that carbonyl oxygen is also within 3 Angstroms of a hydrogen bond donor. Finally, in stage (3) a graph gather is performed solely on the ligand atoms. In certain embodiments, the ligand-only graph gather is made computationally straightforward by the block matrix formulation described above.

In a variety of embodiments, a new set of vector-valued atom types is computed for each atom in a system based on their local network of bonded atoms.

Stage 1:

$$h_i^{(b_1)} = GRU\left(x_i, \sum_e^{N_{et}^{(1)}} \sum_{j \in N^{(e)}(v_i)} NN^{(e)}(x_j)\right) \quad (7)$$

$$\vdots$$

$$h_i^{(b_K)} = GRU\left(h_i^{(b_{K-1})}, \sum_e^{N_{et}^{(1)}} \sum_{j \in N^{(e)}(v_i)} NN^{(e)}\left(h_j^{(b_{K-1})}\right)\right)$$

$$h^{(b)} = \sigma\left(i^{(b)}\left(h^{(b_K)}, x\right)\right) \odot \left(j^{(b)}\left(h^{(b_K)}\right)\right)$$

$$\in \mathbb{R}^{(N \times f_b)}$$

In numerous embodiments, a second stage entails propagation based on both the full adjacency tensor A which begins with the vector-valued atom types $h_i^{(1)}$ computed in (1). While stage (1) computes new bond-based "atom types" for both amino acid and ligand atoms, stage (2) passes both bond and spatial information between the atoms. In certain embodiments, spatial information from a distance matrix is utilized in the second stage in addition to the bond information.

Stage 2:

$$h_i^{(sp_1)} = GRU\left(h_i^{(b)}, \sum_e^{N_{et}^{(2)}} \sum_{j \in N^{(e)}(v_i)} NN^{(e)}\left(h_j^{(b)}, R_{ij}\right)\right) \quad (8)$$

$$\vdots$$

$$h_i^{(sp_K)} = GRU\left(h_i^{(sp_{K-1})}, \sum_e^{N_{et}^{(2)}} \sum_{j \in N^{(e)}(v_i)} NN^{(e)}\left(h_j^{(sp_{K-1})}, R_{ij}\right)\right)$$

$$h^{(sp)} = \sigma\left(i^{(sp)}\left(h^{(sp_K)}, h^{(b)}\right)\right) \odot \left(j^{(sp)}\left(h^{(sp_K)}\right)\right)$$

$$\in \mathbb{R}^{(N \times f_b)}$$

In various embodiments, a graph gather is performed in a third stage (3). Processes in accordance with numerous embodiments of the invention perform the graph gather solely on the ligand atoms.

Stage 3:

$$h^{(FC_0)} = \sum_{j=1}^{N_{Lig}} h_j^{(sp)} \quad (9)$$

$$h^{(FC_1)} = ReLU\left(W^{(FC_1)} h^{(FC_0)}\right)$$

$$\vdots$$

$$h^{(FC_K)} = W^{(FC_K)} h^{(FC_{K-1})},$$

where $i^{(b)}$, $j^{(b)}$, $i^{(sp)}$, $j^{(sp)}$ are bond and spatial neural networks, and $h_j^{(sp)}$ denotes the feature map for the $j^{th}$ atom at the end of stage 2.

More generally, the concepts of incorporating edge information, multiple edge types, distance information, and stages can be summarized in the following formulations, given S stages and that the edge types are treated discretely.

In one formulation in accordance with various embodiments of the invention, each edge type can be treated discretely:

Stage 1:

$$h_i^{(1,1)} = GRU\left(x_i, \sum_e^{N_{et}^{(1)}} \sum_{j \in N^{(e)}(v_i)} NN^{(1,e)}(x_j, R_{ij})\right) \quad (10)$$

$$\vdots$$

$$h_i^{(1,K_1)} = GRU\left(h_i^{(1,K_1-1)}, \sum_e^{N_{et}^{(1)}} \sum_{j \in N^{(e)}(v_i)} NN^{(1,e)}\left(h_j^{(1,K_1-1)}, R_{ij}\right)\right)$$

$$h^{(1)} = \sigma\left(i^{(1)}\left(h^{(1,K_1)}, x\right)\right) \odot \left(J^{(1)}\left(h^{(1,K_1)}\right)\right)$$

$$\in \mathbb{R}^{(N \times f_1)}$$

Stage S:

$$h_i^{(S,1)} = GRU\left(h_i^{(S-1)}, \sum_e^{N_{et}^{(S)}} \sum_{j \in N^{(e)}(v_i)} NN^{(S,e)}\left(h_j^{(S-1)}, R_{ij}\right)\right) \quad (11)$$

$$\vdots$$

$$h_i^{(S,K_S)} = GRU\left(h_i^{(S,K_S-1)}, \sum_e^{N_{et}^{(S)}} \sum_{j \in N^{(e)}(v_i)} NN^{(S,e)}\left(h_j^{(S,K_S-1)}, R_{ij}\right)\right)$$

$$h^{(S)} = \sigma\left(i^{(S)}\left(h^{(S,K_S)}, h^{(S-1)}\right)\right) \odot \left(J^{(S)}\left(h^{(S,K_S)}\right)\right)$$

$$\in \mathbb{R}^{(N \times f_S)}$$

where, for example, $K_S$ defines the number of graph convolutional layers at the S'th stage, $h_i^{(S,K_S)}$ defines the feature map of the i'th atom at stage S after $K_S$ graph convolutional layers, $N_{et}^{(S)}$ denotes the number of edge types to be used at stage S (which is a subset of total number of edge types $N_{et}$), $R_{ij}$ denotes the i'th row and j'th column entry of matrix R (and therefore the distance between atoms/nodes $v_i$ and $v_j$, and $NN^{(S,e)}$ denotes a neural network at stage S for the e'th edge type (though the same neural network can be used for a given edge type at different stages for weight tying), $f_S$ denotes the dimension of the feature map for each atom at the end of stage S. and $i^{(S)}$ and $j^{(S)}$ are gathering neural networks for stage S. It should be noted that, since it was stated that at each stage/set of graph convolutional layers a subset of the edge types and edge information can be utilized, at any given stage, neither the distance information $R_{ij}$, nor soft or hard distance bins, need to be utilized by a given NN within the GRU function. In other words, some of the stages can depend only on bond or other non-spatial relationships between atoms.

In another formulation in accordance with a variety of embodiments of the invention, edge types can be flexible or continuous/dense edge types.

Stage 1:

$$h_i^{(1,1)} = GRU\left(X_i, \sum_{j \in N(v_i)} NN^{(1)}(x_j, R_{ij}, e_{ij})\right) \quad (12)$$

$$\vdots$$

$$h_i^{(1,K_1)} = GRU\left(h_i^{(1,K_1-1)}, \sum_{j \in N(v_i)} NN^{(1)}\left(h_j^{(1,K_1-1)}, R_{ij}, e_{ij}\right)\right)$$

$$h^{(1)} = \sigma\left(i^{(1)}\left(h^{(1,K_1)}, x\right)\right) \odot \left(J^{(1)}\left(h^{(1,K_1)}\right)\right)$$

$$\in \mathbb{R}^{(N \times f_1)}$$

Stage S:

$$h_i^{(S,1)} = GRU\left(h_i^{(S-1)}, \sum_{j \in N(v_i)} NN^{(S)}(h_j^{(S-1)}, R_{ij}, e_{ij})\right) \quad (13)$$

$$\vdots$$

$$h_i^{(S,K_S)} = GRU\left(h_i^{(S,K_S-1)}, \sum_{j \in N(v_i)} NN^{(S)}(h_j^{(S,K_S-1)}, R_{ij}, e_{ij})\right)$$

$$h^{(S)} = \sigma(i^{(S)}(h^{(S,K_S)}, h^{(S-1)})) \odot (j^{(S)}(h^{(S,K_S)}))$$

$$\in \mathbb{R}^{(N \times f_S)}$$

where, for example, $K_S$ defines the number of graph convolutional layers at the S'th stage, $h_i^{(S,K_S)}$ defines the feature map of the i'th atom at stage S after $K_S$ graph convolutional layers, $R_{ij}$ denotes the i'th row and j'th column entry of matrix R (and therefore the distance between atoms/nodes $v_i$ and $v_j$, and $NN^{(S)}$ denotes a neural network at stage S, $e_{ij}$ is a vector denoting either pre-featurized or learned edge features between atoms $v_i$ and $v_j$, $f_S$ denotes the dimension of the feature map for each atom at the end of stage S, and $i^{(S)}$ and $j^{(S)}$ are gathering neural networks for stage S. Although, in the formulations described above, each stage utilizes a distance matrix R, the distance matrix R can be omitted from one or more of the stages. In many embodiments, a first subset of stages may utilize a distance matrix, while a second subset of stages may not involve the distance matrix at all. In some embodiments, the last layer of each stage can simply be set as $h^{(s)} = h^{(s,K_s)}$. Alternatively, or conjunctively, the last layer of each stage in accordance with many embodiments of the invention can be set as $h^{(s)} = NN(h^{(s,K_s)})$ or $h^{(s)} = NN(h^{(s,K_s)}, h^{(s-1)})$ In some embodiments, $e_{ij}$, instead of being pre-defined, can itself be a differentiable function. In one example, $e_{ij}^{(S,3)}$ would be an edge between atoms i and j at Stage S and graph conv layer 3. In this example, $e_{ij}S^{(S,3)} = NN(h_i^{(S,2)}, h_j^{(S,2)})$. In a number of embodiments, $e_{ij}$ can be a neural network dependent on the feature maps of atom i and of atom j at a given stage after a graph convolutional layer in that stage. In some embodiments, $e_{ij}$ can be an RNN. For example, $e_{ij}^{(S,3)} = GRU(e_{ij}^{(S,2)}, W_e^{(S)} \cdot [h_i^{(S,2)}, h_j^{(S,2)}])$.

In the specific case of protein-ligand binding, the graph gather operation would be defined after S stages as:

Gather Stage:

$$h^{(FC_0)} = \sum_{j=1}^{N_{Lig}} h_j^{(S)} \quad (14)$$

$$h^{(FC_1)} = ReLU(W^{(FC_1)} h^{(FC_0)})$$

$$\vdots$$

$$h^{(FC_K)} = W^{(FC_K)} h^{(FC_{K-1})},$$

Figure 2:
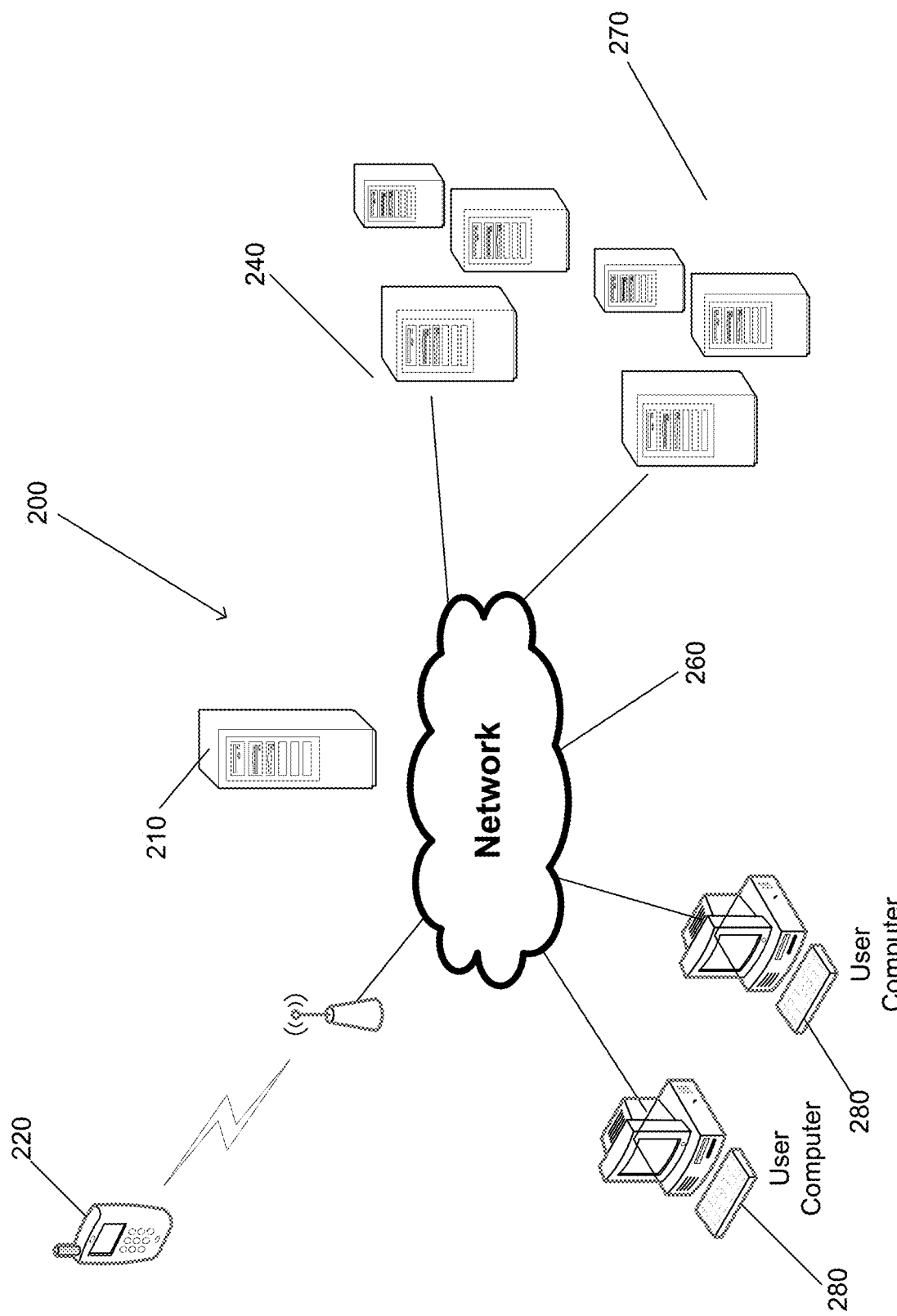
FIG. 2 illustrates a system that provides for modeling and prediction in accordance with some embodiments of the invention.

However, one could replace the sum over $N_{Lig}$ atoms with any subset of the nodes in the graph as appropriate to the requirements of specific applications in accordance with embodiments of the invention. In addition, other types of graph gather neural networks can be used in accordance with some embodiments of the invention, such as replacing the ReLU nonlinearity above with other nonlinearities like sigmoid, Leaky ReLU, tanh, etc. and other operations besides fully connected neural networks can be used, such as recurrent neural networks System and Methods A system that provides for modeling and prediction in accordance with some embodiments of the invention is shown in FIG. 2. Network 200 includes a communications network 260. The communications network 260 is a network such as the Internet that allows devices connected to the network 260 to communicate with other connected devices. Server systems 210, 240, and 270 are connected to the network 260. Each of the server systems 210, 240, and 270 is a group of one or more server computer systems communicatively connected to one another via internal networks that execute processes that provide cloud services to users over the network 260. For purposes of this discussion, cloud services are one or more applications that are executed by one or more server systems to provide data and/or executable applications to devices over a network. The server systems 210, 240, and 270 are shown each having three servers connected via an internal network. However, the server systems 210, 240 and 270 may include any number of servers and any additional number of server systems may be connected to the network 260 to provide cloud services including, but not limited to, virtualized server systems. In accordance with various embodiments of this invention, processes for modeling and predicting molecular properties are provided by one or more software applications executing on a single server system and/or a group of server systems communicating over network 260.

Users may use personal devices 280 and 220 that connect to the network 260 to perform processes for modeling and predicting molecular properties in accordance with various embodiments of the invention. In the illustrated embodiment, the personal devices 280 are shown as desktop computers that are connected via a conventional "wired" connection to the network 260. However, the personal device 280 may be a desktop computer, a laptop computer, a smart television, an entertainment gaming console, or any other device that connects to the network 260 via a "wired" or "wireless" network connection. The mobile device 220 connects to network 260 using a wireless connection. A wireless connection is a connection that uses Radio Frequency (RF) signals, Infrared signals, or any other form of wireless signaling to connect to the network 260. In FIG. 2, the mobile device 220 is a mobile telephone. However, mobile device 220 may be a mobile phone, Personal Digital Assistant (PDA), a tablet, a smartphone, a virtual reality headset, an augmented reality headset, a mixed reality headset or any other type of device that connects to network 260 via wireless connection without departing from this invention. In accordance with some embodiments of the invention, the processes for modeling and predicting molecular properties are performed by the user device. As can readily be appreciated, the specific computing system used to model and predict molecular properties is largely dependent upon the requirements of a given application and should not be considered as limited to any specific computing system(s) implementation.

Figure 3:
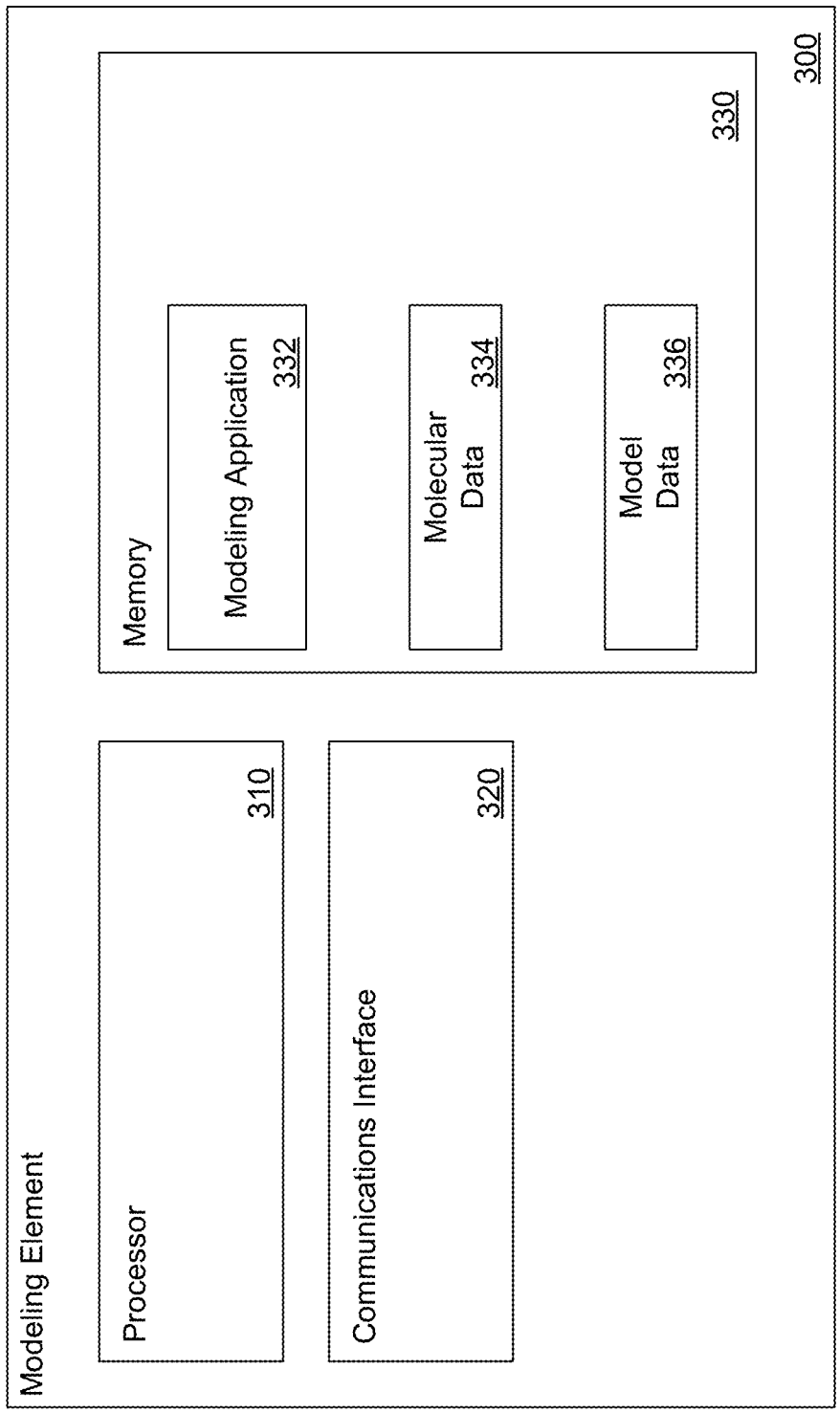
FIG. 3 illustrates a modeling element that provides for modeling and prediction in accordance with some embodiments of the invention.

A modeling element in accordance with several embodiments of the invention is illustrated in FIG. 3. Modeling elements in accordance with many embodiments of the invention can include (but are not limited to) one or more of mobile devices, computers, servers, and cloud services.

Modeling element 300 includes processor 310, communications interface 320, and memory 330.

One skilled in the art will recognize that a particular modeling element may include other components that are omitted for brevity without departing from this invention. The processor 310 can include (but is not limited to) a processor, microprocessor, controller, or a combination of processors, microprocessor, and/or controllers that performs instructions stored in the memory 330 to manipulate data stored in the memory. Processor instructions can configure the processor 310 to perform processes in accordance with certain embodiments of the invention. Communications interface 320 allows modeling element 300 to transmit and receive data over a network based upon the instructions performed by processor 310.

Memory 330 includes a modeling application 332, molecular data 334, and model data 336. Modeling applications in accordance with several embodiments of the invention are used to model and predict the interaction of different molecules. In numerous embodiments, the modeled interactions can be used to identify candidate molecules for further testing. In several embodiments, modeling applications can use molecular data that includes data generated from a variety of sources, including (but not limited to) a molecular simulations and/or a database of molecular properties. Model data 336 in accordance with various embodiments of the invention can include (but is not limited to) data for spatial graphs, edge-type neural networks, and fully-connected classifier networks. Models in accordance with many embodiments of the invention can be used for various purposes, such as (but not limited to) identify feature matrices for each atom of a molecular system and classifying various characteristics of a molecule including, but not limited to binding/non-binding, quantum properties, toxicity, and solubility.

Although a specific example of a modeling element 300 is illustrated in FIG. 3, any of a variety of modeling elements can be utilized to perform processes similar to those described herein as appropriate to the requirements of specific applications in accordance with embodiments of the invention.

Figure 4:
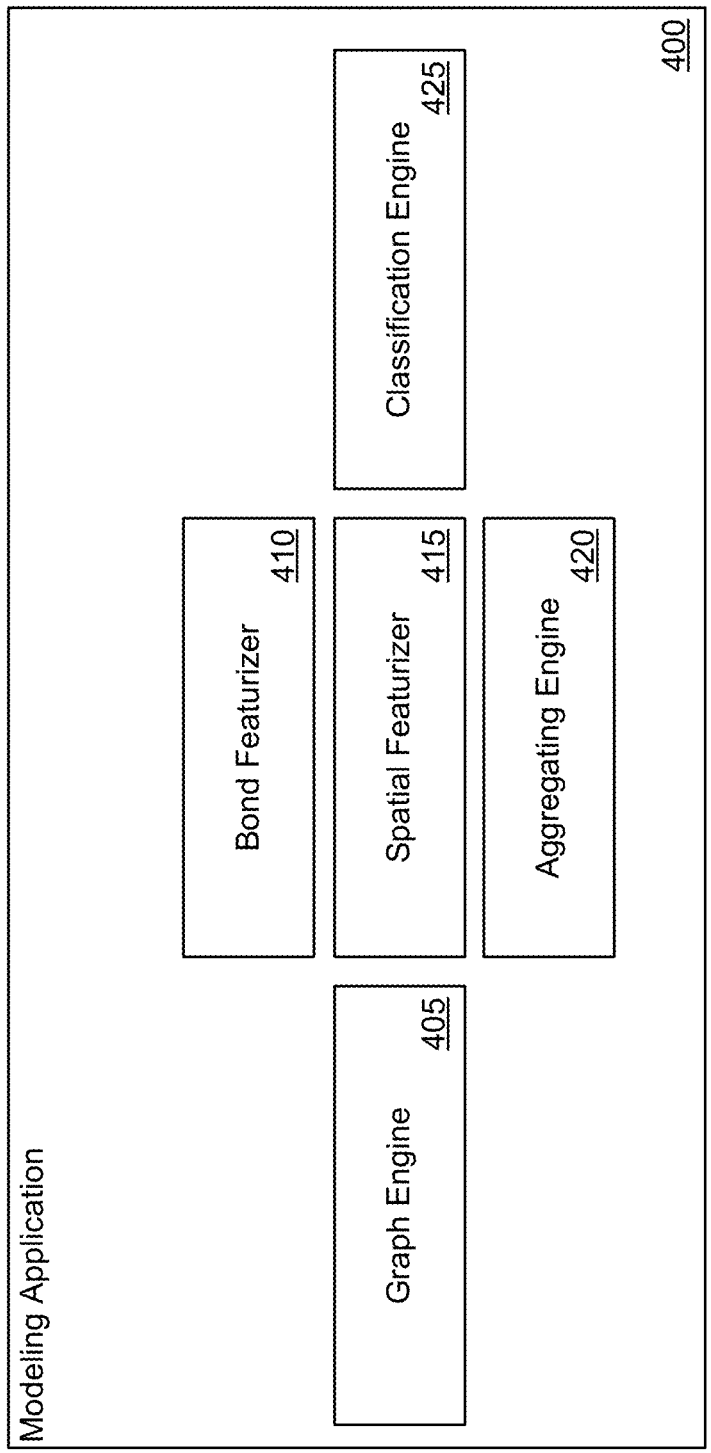
FIG. 4 illustrates a modeling application that provides for modeling and prediction in accordance with some embodiments of the invention.

A modeling application for identifying candidate ligands in accordance with an embodiment of the invention is illustrated in FIG. 4. Modeling application 400 includes graph engine 405, bond featurizer 410, spatial featurizer 415, aggregating engine 420, and classification engine 425. Modeling applications in accordance with many embodiments of the invention can molecular data for a set of molecules of a molecular system to model and predict interactions between the molecules within the system.

In a variety of embodiments, graph engines can build graph representations of a set of molecules. Graph representations can include (but are not limited to) bond information, bond types, distance information, atomic properties, and binding affinities. The constructed graph representations in accordance with a number of embodiments of the invention can include an adjacency matrix and/or a distance matrix.

Bond featurizers in accordance with numerous embodiments of the invention can generate feature matrices for each atom of a molecular system based on the bonds of the atom to each of its neighbors. In numerous embodiments, bond featurizers can operate on different types of bonds at different stages of the modeling and prediction process. In a variety of embodiments, bond featurizers can determine a first set of feature matrices for each atom based on covalent bonds in a first stage, and can be used to determine a second set of feature matrices for the atoms based on other types of bonds. Spatial featurizers in accordance with some embodiments of the invention can generate feature matrices for each atom of a molecular system based on spatial distances between the different atoms, in addition to or in place of the bond types. Bond featurizers in accordance with various embodiments of the invention can operate in conjunction with spatial featurizers in some stages of the process in order to incorporate both bond and spatial information in the feature matrices for each atom. Bond and spatial featurizers can implement a number of neural networks for each bond type and/or for each stage of a process.

Aggregating engines in accordance with various embodiments of the invention can be used to aggregate generated features from the featurizers. In a variety of embodiments, aggregating engines can aggregate a final set of feature matrices generated by bond and/or spatial featurizers. In numerous embodiments, aggregating engines operate only on one of the molecules of a molecular system (e.g., a ligand).

In various embodiments, classification engines can be used to classify or predict an interaction between a set of molecules. Classification engines in accordance with some embodiments of the invention can implement a classifier, such as (but not limited to) a fully connected neural network (FCNN) and/or a random forest. In various embodiments, classification engines take as input a feature matrix generated by featurizers and/or an aggregating engine, and output a likelihood that set of molecules has a particular relationship (e.g., binding/non-binding, agonist/antagonist, etc.). Although a specific example of a modeling application is illustrated in FIG. 4, any of a variety of modeling applications can be utilized to perform processes similar to those described herein as appropriate to the requirements of specific applications in accordance with embodiments of the invention.

Specific examples of a system, element, and application for modeling and predicting molecule characteristics utilizing spatial convolutions in accordance with embodiments of the invention are described above; however, one skilled in the art will recognize that any number of structures and systems can be utilized as appropriate to the requirements of specific applications in accordance with embodiments of the invention.

Figure 5:
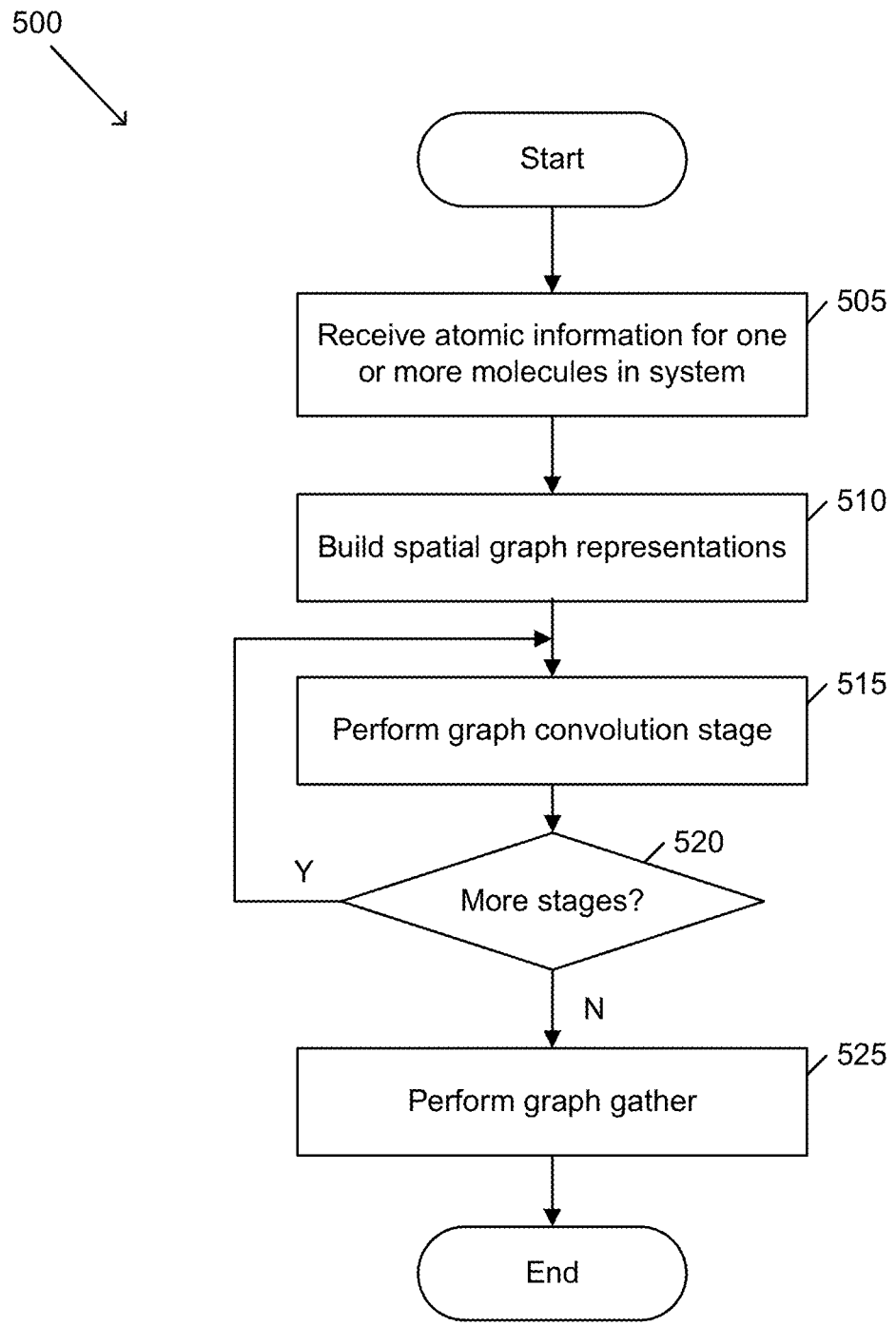
FIG. 5 conceptually illustrates a process for performing a staged convolution in accordance with an embodiment of the invention.

A process for performing a staged convolution in accordance with an embodiment of the invention is conceptually illustrated in FIG. 5. Process 500 receives (505) atomic information for one or more molecules in a system. In a variety of embodiments, the molecules can include a source (e.g., ligand) and a target molecule. Atomic information in accordance with several embodiments of the invention includes various information regarding each molecule, including (but not limited to) distance information and chemical properties. In numerous embodiments, atom types—the $1 \times f_b$ per-atom feature maps—are derived from the same initial features for both ligand and protein atoms. Process 500 builds (510) a spatial graph representation of the ligand and the target molecule. Spatial graph representations in accordance with a variety of embodiments of the invention include a distance matrix and/or an adjacency matrix. Distance matrices in accordance with some embodiments of the invention include distance information for each atom from each other atom in the system. In many embodiments, adjacency matrices include multiple layers (or dimensions), where each layer indicates adjacency along a different edge type. For example, adjacency in a first layer may indicate that two atoms share a covalent bond, while adjacency in a different layer indicates a different bond type. In some embodiments, adjacency does not indicate any particular bond, but whether the two atoms are within a threshold distance of each other.

Processes in accordance with a number of embodiments of the invention can then perform a number of graph convolution stages. Process 500 performs (515) a graph convolution stage. In some embodiments, different graph convolution stages can be based on different subsets of information about the molecular system, where the information can include (but is not limited to) bond type, distance type, and/or other edge type. For example, some stages can be based on solely bond types, while other stages can be based on certain edge types and distance information. A single graph convolution stage in accordance with various embodiments of the invention can be based on a subset of the different edge types, while a different convolution stage is based on a different subset or a complete set of the different edge types. For example, in certain embodiments, an initial graph convolution stage is based on a first layer of an adjacency matrix that indicates the presence of a covalent bond, while a subsequent graph convolution stage is based on all of the bond types as well as atomic distances.

In a number of embodiments, each graph convolution stage produces feature vectors for each atom, learning features for each atom based on the inputs to each stage. Feature vectors in accordance with a variety of embodiments of the invention can be used as inputs to a subsequent graph convolution stage. Each graph convolution stage in accordance with various embodiments of the invention can utilize a set of neural networks. In numerous embodiments, each a separate neural network is trained for each edge type. In many embodiments, neural networks can include, but are not limited to, fully connected neural networks, convolutional networks, and recurrent networks. Neural networks for a particular edge type can be used across the different stages in accordance with various embodiments of the invention in order to tie the weights of the different stages together. However, in many embodiments, a different neural network is trained and utilized for each edge type and stage.

Process 500 determines (520) whether there are more stages to perform. In many embodiments, a specified number of stages are performed. When the process determines that there are more stages to perform, the process returns to step 515. When all of the stages have been completed, process 500 performs (525) a graph gather to aggregate the information after the graph convolution stages. In a number of embodiments, the graph gather is only performed on the atoms of the ligand molecule. In a variety of embodiments, the graph gather step is performed using a fully connected neural network that is trained to predict a classification of the ligand molecule. Classifications can include (but are not limited to) a predicted ability to bind with the target molecule.

Specific processes for classifying atoms utilizing spatial convolutions in accordance with embodiments of the invention are described above; however, one skilled in the art will recognize that any number of processes can be utilized as appropriate to the requirements of specific applications in accordance with embodiments of the invention.

Figure 6:
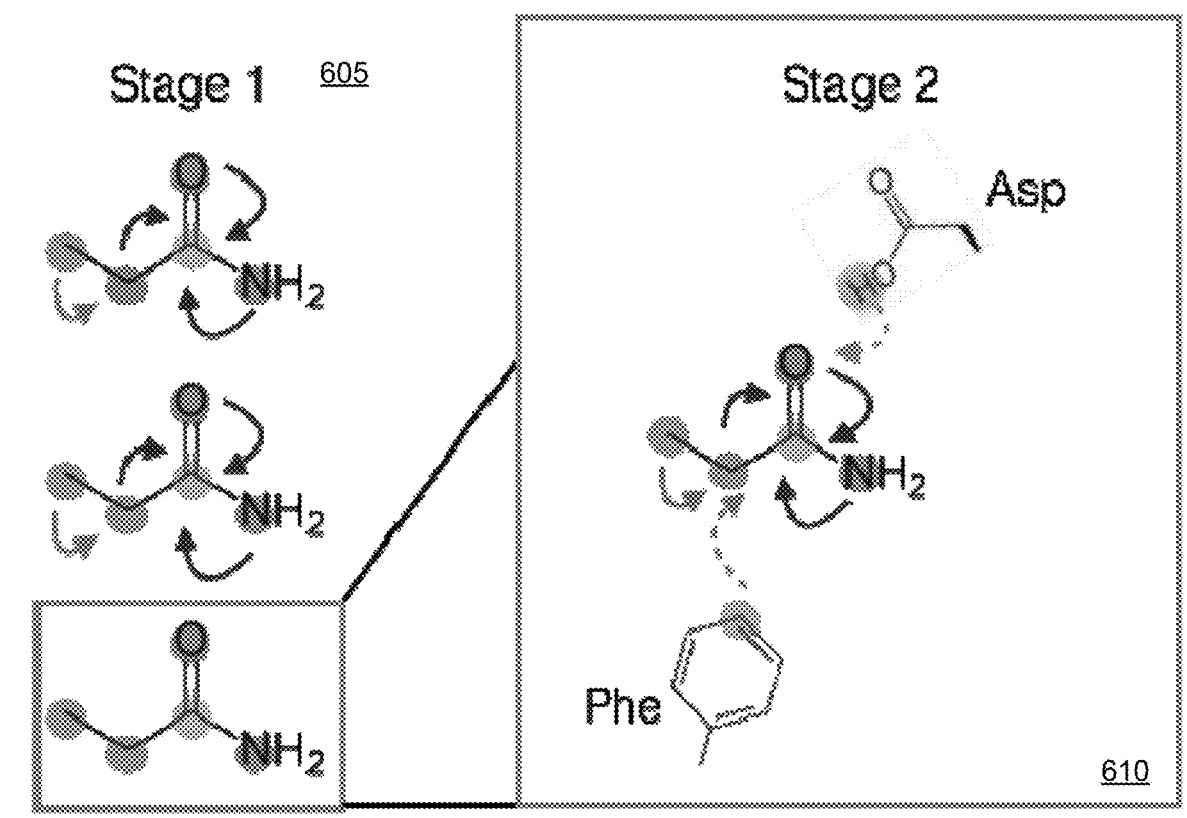
FIG. 6 illustrates a visual depiction of a multi-staged spatial gated graph neural network.

A visual depiction of a multi-staged spatial gated graph neural network in accordance with various embodiments of the invention is illustrated in FIG. 6. The first stage 605 entails graph convolutions over only bonds, which derives new node (atom) feature maps roughly analogous to differentiable atom types in more traditional forms of molecular modeling. The second stage 610 entails both bond-based and spatial distance based propagation of information. In the third stage 615, a graph gather operation is conducted over the ligand atoms, whose feature maps are derived from bonded ligand information and spatial proximity to protein atoms. In contrast to molecular dynamics force fields, which—for historical reasons—have distinct force fields for ligands and for proteins which then must interoperate (often poorly) in simulation, processes in accordance with some embodiments of the invention can derive the physicochemical properties of biomolecular interactions from a unified framework.

Figure 7:
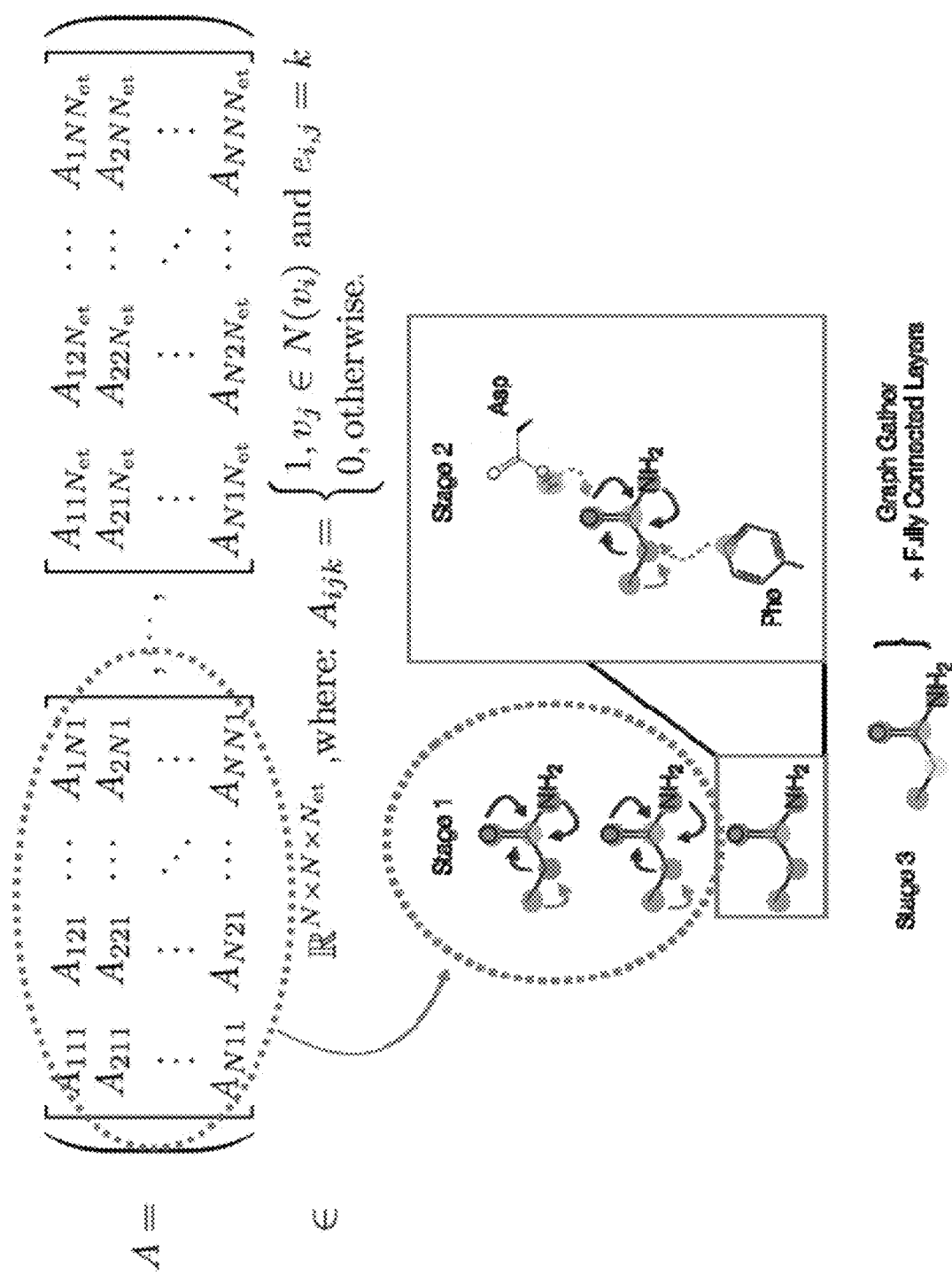
FIG. 7 illustrates a first stage of a multi-staged spatial gated graph neural network in accordance with a variety of embodiments of the invention.
Figure 8:
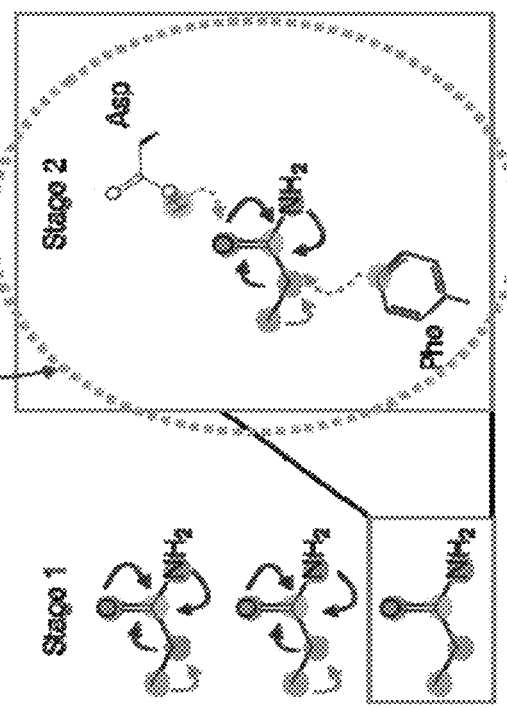
FIG. 8 illustrates a second stage of a multi-staged spatial gated graph neural network in accordance with a variety of embodiments of the invention.

To further illustrate, the first and second stages in accordance with various embodiments of the invention exploit different subsets of the full adjacency tensor A. A first stage in accordance with a variety of embodiments of the invention is illustrated in FIG. 7. In this example, only covalent or bonded interaction edge types encoded in the first slices of the last dimension of the adjacency tensor A are exploited. The second stage in accordance with a number of embodiments of the invention is illustrated in FIG. 8. In this example, both bonded and non-bonded interaction edge types spanning the entirety of the last dimension of the adjacency tensor A are exploited. In a variety of embodiments, the second stage can also include spatial data that describes a distance between the various atoms.

Traditional metrics of predictor performance suffer from general problems and drug discovery-specific issues. For regressors, both $R^2$—the "coefficient of determination"—and the root-mean-square error (RMSE) are susceptible to single data point outliers. The RMSE for both classifiers and regressors account for neither the training data distribution nor the null model performance. The area under the receiver operating characteristic curve can correct this deficiency in RMSE for classifiers. However, all aforementioned metrics are global statistics that equally weight all data points. This property is particularly undesirable in drug discovery, which is most interested in predicting the tails of a distribution: while model predictions are made against an entire library containing millions of molecules, one will only purchase or synthesize the top scoring molecules.

In response, the cheminformatics community has adopted the concept of early enrichment, weighting the importance of the model's highest performers more heavily. At present, this progress in early enrichment measurement has been limited to classification and has yet to include regression. Processes in accordance with numerous embodiments of the invention utilize a new metric for early enrichment in regression. $EF_\chi^{(R)}$, analogous to $EF_\chi$. For a given target:

$$EF_\chi^{(R)} = \frac{1}{\chi \cdot N} \sum_i^{\chi \cdot N} \frac{y_i - \bar{y}}{\sigma(y)} = \frac{1}{\chi \cdot N} \sum_i^{\chi \cdot N} z_i, \tag{15}$$

in which $y_i$, the experimental (observed) measurement for sample i, are ranked in descending order according to $\hat{y}_i$, the model (predicted) measurement for sample i. In other words, the average z-score for the observed values of the top $\chi\%$ scoring samples is computed, rather than computing, for example, $$\frac{1}{\chi \cdot N} \sum_i^{\chi \cdot N} (y_i - \bar{y}),$$

which has units that are the same as $y_i$ (i.e., $\log(K_i)$ values). Unfortunately, this unnormalized approach depends on the distribution in the dataset. For instance, in a distribution of $\log(K_i)$ measurements, if the maximum deviation from the mean is 1.0, the best a model can possibly perform would be to achieve an $EF_\chi^{(R)}$ of 1.0.

Processes in accordance with various embodiments of the invention normalize through division by $\sigma(y)$, the standard deviation of the data. This can allow for comparison of model performance across datasets with a common unit of measurement but different variances in those measurements. The upper bound is therefore equal to the right hand side of (15), where the indexed set of molecules i constitutes the subset of the $\chi \cdot N$ most experimentally active molecules. This value is dependent on both the distribution of the training data as well as the value $\chi$. The $EF_\chi^{(R)}$ is an average over $\chi \cdot N$ z-scores, which themselves are real numbers of standard deviations away from the mean experimental activity. $EF_\chi^{(R)}$ values may therefore exceed 1.0, since this means that the $\chi$ percentage of top predicted molecules have an average standard deviation of more than 1.0 above the mean.

Spatial graph convolutions exhibit state-of-the-art performance in affinity prediction. Spatial graph convolutions in accordance with several embodiments of the invention use a more principled deep learning approach. Input features are only basic information about atoms, bonds, and distances. In various embodiments, this framework does not use traditional hand-crafted features, such as hydrophobic effects, n-stacking, or hydrogen bonding. Instead, higher-level interaction "features" in accordance with various embodiments of the invention are learned through intermediate graph convolutional neural network layers. Despite the simpler input featurization, spatial graph convolutions in accordance with various embodiments of the invention can learn an accurate mapping of protein-ligand structures to binding free energies using the same relatively low amount of data as previous expertise-driven approaches. If machine learning is to be applied to real-world drug discovery settings it is imperative to measure a given model's capacity both to interpolate within familiar regions of chemical space as well as to generalize to its less charted territories.

In an aspect, the present disclosure provides methods and systems for predicting characteristics for molecules. The method comprises, (a) obtaining a representation of a set of molecules as a graph with N atoms and $N_{et}$ edge types; (b) performing a first set of graph convolutions with a graph representation of a set of molecules with a subset of the $N_{et}$ edge types; (c) performing between 0 and S−1 further sets of graph convolutions each with a subset of the $N_{et}$ edge types; and (d) if characteristic prediction is desired, performing a graph gather over a subgraph of the graph followed by further neural network layers.

The system comprises one or more processors that are individually or collectively configured to, (a) obtain a representation of a set of molecules as a graph with N atoms and $N_{et}$ edge types; (b) perform a first set of graph convolutions with a graph representation of a set of molecules with a subset of the $N_{et}$ edge types; (c) perform between 0 and S−1 further sets of graph convolutions each with a subset of the $N_{et}$ edge types; and (d) if characteristic prediction is desired, perform a graph gather over a subgraph of the graph followed by further neural network layers.

In some embodiments, a representation of a set of molecules further comprises an N×N distance matrix. The $N_{et}$ edge types can comprise bond types, salt bridges, pi stacking, distance bins, a distance basis set, raw distances, or a combination thereof. In some embodiments, (b) further comprises incorporating information directly from the N×N distance matrix. In some embodiments, (c) further comprises performing graph convolutions with the N×N distance matrix. In some embodiments, the subgraph of a graph can be of one or more of the molecules.

In some embodiments, the subgraph of a graph can be 1 subgraph, 2 subgraphs, 3 subgraphs, 4 subgraphs, 5 subgraphs, or more. In some embodiments, the subgraph of a graph can be 1 to 1000000 subgraphs, 1 to 10000 subgraphs, 1 to 1000 subgraphs, 1 to 100 subgraphs, 1 to 50 subgraphs, 1 to 20 subgraphs, 1 to 10 subgraphs, or 1 to 5 subgraphs.

In an aspect, the present disclosure provides a method for predicting characteristics for molecules. The method comprises: (a) performing a first set of graph convolutions with a spatial graph representation of a set of molecules, wherein the first set of graph convolutions are based on bonds between the set of molecules; (b) performing a second set of graph convolutions with the spatial graph representation, wherein the second set of graph convolutions are based on at least a distance between each atom and other atoms of the set of molecules; (c) performing a graph gather with the spatial graph representation; and (d) predicting a set of one or more characteristics for the set of molecules. The set of molecules, can be 1 molecule, 2 molecules, or more molecules.

In some embodiments, predicting a set of one or more characteristics comprises assessing data from the graph gather. Processes in accordance with numerous embodiments of the invention can receive atomic information for the set of one or more molecules. The atomic information can be but is not limited to: bond lengths within a molecule, bond strengths within a molecule, bond angles within a molecule, dihedral angles within a molecule, dihedral angles between two and/or more molecules, bond angles between two and/or more molecules, interatomic distances between pairs of atoms of the same or of two and/or more different molecules, interatomic angles between triples of atoms of the same or two and/or more different molecules), bond distances between two and/or more molecules, the charge of a molecule, electronegativity of a molecule, the dipole of a given pair of atoms, the dipole of a molecule, the dipole of a set of one or more molecules, and/or forces between two and/or more molecules. Forces between two and/or more molecules can be but are not limited to: electrostatic, ionic attraction, intermediate dipole-dipole, weak London dispersion, hydrophobic interaction, hydrophilic interaction, van der Waal's, hydrogen bonding, covalent bonding, metallic bonding, magnetic, and/or physical. The atomic information of an atom or atoms within a molecule can be include but is not limited to: the chemical element, atomic number, number of protons, number of electrons, approximate mass, electric charge, diameter, shape, orbital shape, size, energy levels, valency, magnetic moment, and/or isotope.

In a variety of embodiments, building the spatial graph representation can comprise generating a distance matrix and an adjacency tensor wherein the distance matrix denotes distances between atoms of the set of molecules and the adjacency tensor indicates a plurality of different edge types between atoms. Edge types can include but are not limited to: covalent bonds, ionic bonds, polar bonds, metallic bonds, non-covalent bonds (e.g. π-π stacking), salt bridge, distance bins (hard cutoff and/or expanded in a Gaussian and/or other basis set), and/or hydrogen bonds.

In many embodiments, the set of molecules comprises a ligand molecule and a target molecule, wherein rows of the distance matrix are ordered by membership in the ligand and target molecules.

In some embodiments, the bonds between the set of molecules comprise covalent bonds. In numerous embodiments, bonds between the set of molecules comprise at least one of π-π stacking, hydrogen bonds, and hydrophobic contact. In some embodiments, the bonds/edges between the atoms in different molecules in the set comprise of distances in soft or hard bins. In some embodiments, the set of molecules can comprise one molecule. In some embodiments, the set of molecules can comprise one molecule surrounded by solvent molecules.

In some embodiments, the second set of graph convolutions are further based on bonds between the set of molecules. In some embodiments, the first set of graph convolutions can be based on a first set of the bonds between the set of molecules and the second set of graph convolutions can be based on a second set of the bonds between the set of molecules. In some embodiments, the first set of bonds is a subset of the second set of bonds.

Performing the first set of graph convolutions in accordance with many embodiments of the invention comprises performing an operation at each layer of the graph convolutions. In some embodiments, the operation can be, but is not limited to: gated recurrent unit (GRU), long short-term memory (LSTM), gated linear unit (GLU), recurrent neural network, fully connected neural networks, or a combination thereof. In a number of embodiments, performing the first set of graph convolutions comprises performing a gated recurrent unit (GRU) operation at each layer of the graph convolutions.

In several embodiments, performing the first set of graph convolutions comprises utilizing a first plurality of neural networks, wherein each neural network of the plurality of neural networks can be used for a different bond type. In a number of embodiments, performing the second set of graph convolutions comprises utilizing a second plurality of neural networks, wherein weights for the first plurality of neural networks can be shared with the second plurality of neural networks.

In several embodiments, performing the second set of graph convolutions comprises utilizing a second plurality of neural networks, wherein the neural networks of the second plurality of neural networks can utilize distance information regarding distances between atoms of the set of molecules.

In some embodiments, the set of molecules comprises a ligand molecule and a target molecule, wherein the graph gather can be performed solely on the ligand molecule.

In some embodiments, the set of characteristics comprises whether a first molecule of the set of molecules binds with a second molecule of the set of molecules.

In another aspect, the present disclosure provides a method for training a spatial convolution graph model. The method comprises: performing a first set of graph convolutions with a spatial convolution graph model of a set of molecules, wherein the first set of graph convolutions are based on bonds between the set of molecules; performing a second set of graph convolutions with the spatial convolution graph model, wherein the second set of graph convolutions are based on at least a distance between each atom and other atoms of the set of molecules; performing a graph gather with the spatial convolution graph model; computing loss for the set of molecules; and updating the spatial convolution graph model based on the computed loss.

In some embodiments, predicting motion of the set of molecules can be calculated by conducting stochastic simulations, for example, estimating solvation effects, estimating conformational entropy, exploring different conformations of both the protein and the ligand (e.g., the "induced fit" model of binding). Predicting motion in accordance with several embodiments of the invention can be used to simulate key biophysical processes, such as (but not limited to) ligand binding to a protein), which can depend on several properties that can be calculated by predicting the motion of a set of molecules.

In certain embodiments, processes and systems can use layers of the spatial convolution graph model to train a set of one or more neural networks to predict a set of one or more parameters for a force field. Layers of the network can train a set of 1, 2, 3, 4, 5, 10, 20, 50, 100, 1000, 10000 or more neural networks to predict a set of one or more parameters for a force field. Layers of the network can train a set of 1-10000, 1-1000, 1-500, 1-100, 1-10, or 1-5 neural networks to predict a set of one or more parameters for a force field. Neural networks can be used to predict a set of 1, 2, 3, 4, 5, 10, 20, 50, 100, 1000, 10000 or more parameters for a force field. Neural networks can be used to predict a set of 1-10000, 1-1000, 1-500, 1-100, 1-10, or 1-5 parameters for a force field.

In various embodiments, the set of parameters can be associated with a set of one or more characteristics, the set of characteristics include at least one of charges, bonds angles, and dihedrals. The set of parameters can be associated with a set of 1, 2, 3, 4, 5, 10, 20, 50, 100, 1000, 10000 or more characteristics. The set of parameters can be associated with a set of 1-10000, 1-1000, 1-500, 1-100, 1-10, or 1-5 characteristics.

In certain embodiments, the spatial convolution graph model can be a first spatial convolution graph model, the method further comprises: training a second spatial convolution graph model to predict potential energy; and predicting a potential energy of a molecular system based on the first and second spatial convolution graph models.

In various embodiments, training the second spatial convolution graph model comprises sharing a set of one or more layers between the first and second spatial convolution graph models. Training the second spatial convolution graph model can comprise sharing a set of 1, 2, 3, 4, 5, 10, 20, 50, 100, 1000, 10000 or more layers between the first and second spatial convolution graph models. Training the second spatial convolution graph model can comprise sharing a set of 1-10000, 1-1000, 1-500, 1-100, 1-10, or 1-5 layers between the first and second spatial convolution graph models.

In some embodiments, the force field is an Assisted Model Building with Energy Refinement (AMBER) functional form. In some embodiments, the force field functional can be a fully neural potential and can take on the characteristics of a fixed form potential such as but not limited to AMBER, CHARMM (with or without CMAP terms), GROMOS, AMOEBA, or a combination thereof.

In numerous embodiments, systems and processes can use layers of the spatial convolution graph model to train a set of one or more neural networks to predict a potential energy of an input molecular system. Layers of the spatial convolution graph model can be used to train a set of 1, 2, 3, 4, 5, 10, 20, 50, 100, 1000, 10000 or more neural networks to predict a potential energy of an input molecular system. Layers of the spatial convolution graph model can be used to train a set of 1-10000, 1-1000, 1-500, 1-100, 1-10, or 1-5 neural networks to predict a potential energy of an input molecular system.

In various embodiments, identifying a set of conformations of the set of molecules by minimizing the potential energy predicted by the spatial graph convolution model.

In another aspect, the present disclosure provides a system for predicting characteristics for molecules, comprising: one or more processors that are individually or collectively configured to perform a first set of graph convolutions with a spatial graph representation of a set of molecules, wherein the first set of graph convolutions are based on bonds between the set of molecules: perform a second set of graph convolutions with the spatial graph representation, wherein the second set of graph convolutions are based on at least a distance between each atom and other atoms of the set of molecules; perform a graph gather with the spatial graph representation; and predict a set of one or more characteristics for the set of molecules.

In another aspect, the present disclosure provides methods and systems for drug discovery. The methods may comprise identifying a candidate ligand from predicted molecular characteristics with machine learning. In some embodiments, identifying a candidate ligand comprises executing a first set of graph convolutions with a spatial graph representation of a set of molecules, wherein the first set of graph convolutions are based on bonds between the set of molecules; executing a second set of graph convolutions with the spatial graph representation, wherein the second set of graph convolutions are based on at least a distance between each atom and other atoms of the set of molecules; performing a graph gather with the spatial graph representation; predicting a set of one or more characteristics for the set of molecules; and predicting the candidate ligand from the set of one or more characteristics for the set of molecules.

In some embodiments, the system comprises the one or more processors that are individually or collectively configured to: execute a first set of graph convolutions with a spatial graph representation of a set of molecules, wherein the first set of graph convolutions are based on bonds between the set of molecules; execute a second set of graph convolutions with the spatial graph representation, wherein the second set of graph convolutions are based on at least a distance between each atom and other atoms of the set of molecules; execute a graph gather with the spatial graph representation; predict a set of one or more characteristics for the set of molecules; and predict the candidate ligand from the set of one or more characteristics for the set of molecules.

In some embodiments, the set of one or more characteristics comprises binding affinity. In some embodiments, the set of one or more characteristics comprises ligand conformation. In some embodiments, the set of one or more characteristics can be charge of the ligand, toxicity, absorption, distribution, metabolism, elimination, CYP450 subtype inhibition, metabolic stability, membrane permeability, oral bioavailability, quantum electronic properties, solubility, Log D, or a combination thereof.

In some embodiments, a pre-trained model may be utilized to assist in predicting a candidate ligand from the set of one or more characteristics for the set of molecules.

In a variety of embodiments, to compare performance of the proposed architectures to previous methods the performance was evaluated based on PDBBind 2007. In some embodiments, the PDBBind 2007 dataset was split by (a) beginning with the "refined" set comprising protein-ligand co-crystal structures and associated binding free energy values; (b) removing the "core" set to form the test set, with (c) the remaining samples serving as the training data. In the present disclosure, this train-test split refers to "PDBBind 2007. Refined Train, Core Test", below, and compare performance with RF-score, X-Score and the networks described in this present disclosure.

In the present disclosure, the disclosure investigates a cross-validation strategy that, in some embodiments, splits all of the training data into three distinct folds-train, validation, and test subsets—with hierarchical clustering based on pairwise structural and sequence homology as distance metrics. In a variety of embodiments, cross-validation for benchmarking uses a hyperparameter set.

Examples

The following examples are offered to illustrate, but not to limit the claimed invention. The performance of deep neural network algorithms is highly sensitive to chosen hyper-parameters. Such sensitivity underscores the criticality of rigorous cross-validation. In order to compare performance of the proposed architectures to previous methods the performance was evaluated based on PDBBind 2007. In previous works, the PDBBind 2007 dataset was split by (a) beginning with the "refined" set comprising 1,300 protein-ligand co-crystal structures and associated binding free energy values; (b) removing the "core" set comprising 195 samples to form the test set, with (c) the remaining 1,095 samples serving as the training data. In the present disclosure, this train-test split refers to "PDBBind 2007, Refined Train. Core Test", below, and compare performance with RF-score, X-Score and the networks described in this present disclosure.

In the present disclosure, the disclosure investigates a cross-validation strategy that, in some embodiments, splits all of the training data into three distinct folds—train, validation, and test subsets—with hierarchical clustering based on pairwise structural and sequence homology as distance metrics. On the standard PDBBind 2007 "refined train, core test" benchmark, Spatial Graph Convolutions achieve state-of-the-art performance as reflected by several metrics. PotentialNet outperforms RF-Score and X-Score according to Pearson and Spearman correlation coefficients. The Pearson correlation score for (7)-(14) is within error of the reported score for TopologyNet, the heretofore top performing model on this benchmark. Cross-validation for this including all of the results reported in Tables I, II, and III, was performed such that performance on the test set was recorded for the hyperparameter set that performed most highly on the distinct validation set (Table VII). In contrast, the TopologyNet, models were trained on a combination of the validation and training sets and evaluated directly on the test set. Performance for TopologyNet therefore reflects a train-validation type split rather than a train-validation-test split, which likely inflated the performance of that method. Tables IV-VI illustrate comparative results for predictions of quantum properties, toxicity, and solubility.

TABLE I

Benchmark: PDBBind 2007, Refined Train, Core Test

| Model | Test $R^2$ | Test $EF\chi^{(R)}$ | Test Pearson | Test Spearman | Test stdev | Test MUE |
|---|---|---|---|---|---|---|
| PotentialNet | 0.668 (0.043) | 1.643 (0.127) | 0.822 (0.021) | 0.826 (0.020) | 1.388 (0.070) | 0.626 (0.037) |
| PotentialNet, (ligand-only control) | 0.419 (0.234) | 1.404 (0.171) | 0.650 (0.017) | 0.670 (0.014) | 1.832 (0.135) | 0.839 (0.005) |
| TopologyNet, No Valid. Set | N/A | N/A | 0.826 | N/A | N/A | N/A |
| RF-Score | N/A | N/A | 0.783 | 0.769 | N/A | N/A |
| X-Score | N/A | N/A | 0.643 | 0.707 | N/A | N/A |

TABLE II

Benchmark: PDBBind 2007 Refined, Agglomerative Sequence Split

| Model | Test $R^2$ | Test $EF\chi^{(R)}$ | Test Pearson | Test Spearman | Test MUE |
|---|---|---|---|---|---|
| PotentialNet | 0.480 (0.030) | 0.867 (0.036) | 0.700 (0.003) | 0.694 (0.012) | 1.680 (0.061) |
| Ligand-only PotentialNet | 0.414 (0.058) | 0.883 (0.025) | 0.653 (0.031) | 0.674 (0.020) | 1.712 (0.110) |
| RF-score | 0.527 (0.014) | 1.078 (0.143) | 0.732 (0.009) | 0.723 (0.013) | 1.582 (0.034) |
| X-score | 0.470 | 1.117 | 0.702 | 0.764 | 1.667 |

TABLE III

Benchmark: PDBBind 2007 Refined, Agglomerative Structure Split

| Model | Test $R^2$ | Test $EF\chi^{(R)}$ | Test Pearson | Test Spearman | Test MUE |
|---|---|---|---|---|---|
| PotentialNet | 0.629 (0.044) | 1.576 (0.053) | 0.823 (0.023) | 0.805 (0.019) | 1.553 (0.125) |
| Ligand-only PotentialNet | 0.500 (0.010) | 1.498 (0.411) | 0.733 (0.007) | 0.726 (0.005) | 1.700 (0.067) |
| RF-score | 0.594 (0.005) | 0.869 (0.090) | 0.779 (0.003) | 0.757 (0.005) | 1.542 (0.046) |
| X-score | 0.517 | 0.891 | 0.730 | 0.751 | 1.751 |

TABLE IV

Quantum Property Prediction with QMS Dataset

| Network | Valid MAE | Test MAE |
|---|---|---|
| Spatial PotentialNet, Staged | 0.0120 | 0.0118 (0.0003) |
| Spatial PotentialNet, SingleUpdate | 0.0133 | 0.0131 (0.0001) |
| MPNN | 0.0142 | 0.0139 (0.0007) |
| DTNN | 0.0168 | 0.0163 (0.0010) |

TABLE V

Toxicity Prediction with the Tox21 Dataset

| Network | Valid ROC AUC | Test ROC AUC |
|---|---|---|
| PotentialNet | 0.878 | 0.857 (0.006) |
| Weave | 0.852 | 0.831 (0.013) |
| GraphConv | 0.858 | 0.838 (0.001) |
| XGBoost | 0.778 | 0.808 (0.000) |

TABLE VI

Solubility Prediction with the Delaney ESOL Dataset

| Network | Valid RMSE | Test RMSE |
|---|---|---|
| PotentialNet | 0.517 | 0.490 (0.014) |
| Weave | 0.549 | 0.553 (0.035) |
| GraphConv | 0.721 | 0.648 (0.019) |
| XGBoost | 1.182 | 0.912 (0.000) |

TABLE VII

Hyperparameters for PotentialNet neural networks

| Network | Hyperparameter Name | Symbol | Possible Values |
|---|---|---|---|
| PotentialNet | Gather Widths (Bond and Spatial) | $f_{bond}$, $f_{spatial}$ | [64, 128] |
| PotentialNet | Number of Bond Convolution Layers | $bond_K$ | [1, 2] |
| PotentialNet | Number of Spatial Convolution Layers | $spatial_K$ | [1, 2, 3] |
| PotentialNet | Gather Width | $f_{gather}$ | [64, 128] |
| PotentialNet | Number of Graph Convolution Layers | K | [1, 2, 3] |
| Both | Fully Connected Widths | $n_{rows}$ of $W^{(FC_i)}$ | [[128, 32, 1], [128, 1], [64, 32, 1], [64, 1]] |
| Both | Learning Rate | — | [1e-3, 2e-4] |
| Both | Weight Decay | — | [0., 1e-7, 1e-5, 1e-3] |
| Both | Dropout | — | [0., 0.25, 0.4, 0.5] |

These examples are offered to illustrate, but not to limit the claimed invention.

Molecular Dynamics with Spatial Graph Convolutions

While the neural network community invests increasing resources into generative models, such as generative adversarial networks (GANs) and variational autoencoders (VAEs), the natural sciences has been working on a family of generative models since the seventeenth century: physics. Optical physics precludes the observation of real-time, atomic-resolution behavior of biological macromolecules and the small molecule drugs that bind to them. While quantum mechanics (QM) places fundamental limits on such experimental observation, knowledge of its mathematical framework also confers the ability to theoretically model such atomistic behavior with arbitrary degrees of precision.

First Newtonian mechanics, predicated on three laws of motion and simple inverse-square-law potentials, enabled incredibly precise predictions of the future positions of objects given initial conditions. In the twentieth century, as measurement of micro- and nanoscale phenomena became more prevalent, quantum mechanics was invented to realize unprecedented accuracy in predicting the long-term, if stochastic, behavior of subatomic, atomic, and molecular systems.

Molecular dynamics (MD) is a family of techniques that renders such theoretical illumination of molecules more computationally tractable than pure QM by making Newtonian approximations to the underlying Schrodinger equation. Two fundamental tradeoffs exist in the examination of molecular systems: the tradeoff between spatial and temporal resolution in the experimental observation of molecules, and the tradeoff between the speed and accuracy of computational methods that explicitly model all atoms in a system. Molecular dynamics is a type of simulation that uses Newtonian mechanics to approximate the more realistic yet slower-to-evaluate physical models embodied in quantum mechanics. Inaccuracies in molecular dynamics mainly stem from force field error—inaccuracies in the potential energy function based on positions of the atoms in the system—and from insufficient timescales of simulation.

Systems and methods in accordance with several embodiments of the invention provide frameworks for developing more accurate estimations of energy, and therefore of force field, for molecular systems. Processes in accordance with a number of embodiments of the invention deploy spatial graph convolutions to reparameterize the Assisted Model Building with Energy Refinement (AMBER) functional form to more accurately represent the behavior of small organic molecules. Processes in accordance with some embodiments of the invention can automatically generate new parameters for any given query biomolecular system, from individual amino acids and bases to proteins and nucleic acids. In certain embodiments, processes can deploy graph convolutions to train a new force field based on the AMBER functional form that has dominated MD simulations in recent decades. In a number of embodiments, deep neural networks (DNN's) can be utilized to learn a new functional form that computes energy based on differentiable, learned atom types stemming from fixed, simple initial featurizations and the dynamic relative positions of the atoms. In certain embodiments, a potential energy function can be constructed and evaluated based on spatial graph convolutions, such as those described above. Graph convolutional potential (GCP) models in accordance with certain embodiments of the invention can be trained and evaluated on a dataset consisting of high-level quantum mechanical calculations of energy for multiple conformers of a set of small molecules. The gradient of this energy function as computed with backpropagation in accordance with a variety of embodiments of the invention can form the basis for even more accurate molecular dynamics simulations unconstrained by the inherent limitations of the AMBER functional form.

The highly prevalent AMBER functional form is fit in the AMBER and CHARMM force fields using a combination of quantum mechanical calculations, NMR, and other empirical data. The functional form is described as below:

$$V(r^N) = \sum_{bonds} k_b(l - l_0)^2 + \sum_{angles} k_a(\theta - \theta_0)^2 + \sum_{torsions} \sum_n \frac{1}{2} V_n[1 + \cos(n\omega - \gamma)] + \sum_{j=1}^{N-1} \sum_{i=j+1}^{N} f_{ij} \left\{ \varepsilon_{ij} \left[ \left(\frac{r_{0ij}}{r_{ij}}\right)^{12} - 2\left(\frac{r_{0ij}}{r_{ij}}\right)^{6} \right] + \frac{q_i q_j}{4\pi\varepsilon_0 r_{ij}} \right\} \quad (16)$$

The scalar output $V(r^N)$ is a potential energy that is a function of the positions of the atoms, the "types" of atoms, and the parameters associated with those atoms and 2-tuples (bonds, van Der Waals forces, electrostatic forces), 3-tuples (angles), and 4-tuples (dihedrals) thereof. In some embodiments, a neural network is trained. Neural networks in accordance with several embodiments of the invention can take as input initial feature tensors (x,A,R) and compute the parameters in (16) to most accurately compute potential energy, where x is an $N \times f_{in}$ matrix where each of the N atoms is represented by a row vector of $f_{in}$ features; A is an $N \times N \times N_{et}$ tensor of adjacency matrices among $N_{et}$ edge types (bond types, noncovalent interactions, etc.), and R is an $N \times N$ distance matrix.

In certain embodiments, processes can derive dense, differentiable feature maps for each atom analogous to the discrete "atom types" in traditional force fields. In some such embodiments, a dataset (such as the ANI-1 dataset) can be utilized to fit a new AMBER-like force field (FF) that applies the "featurization" (charges, equilibrium bond lengths, angles, dihedrals, and force constants thereof) to amino acids and small molecules thereof based on its training on the dataset. The recently published ANI-1 dataset comprises approximately 20 million total conformations spread across approximately 60,000 small organic molecules and associated energy values as computed through density functional theory (DFT), a quantum chemistry method. In certain embodiments, force fields, either based strictly on a fully PotentialNet or graph convolutional potential or an AMBER functional form whose parameters are derived from graph convolutions, can be trained with data from Quantum Chemistry calculations (e.g., the ANI-1 dataset), NMR experimental data, etc. For a given small molecule, x and A will be fixed but R will vary for each conformer. Spatial graph convolutions in accordance with many embodiments of the invention can learn atom-level features, where these atom-level features are continuous, differentiable analogs to the "atom types" common in traditional force fields.

Stage 1:

$$h_i^{(1,1)} = GRU\left(x_i, \sum_e \sum_{j \in N^{(e)}(v_i)}^{N_{et}^{(1)}} NN^{(1,e)}(x_j, R_{ij})\right) \quad (17)$$

$$\vdots$$

$$h_i^{(1,K_1)} = GRU\left(h_i^{(1,K_1-1)}, \sum_e \sum_{j \in N^{(e)}(v_i)}^{N_{et}^{(1)}} NN^{(1,e)}\left(h_j^{(1,K_1-1)}, R_{ij}\right)\right)$$

$$h^{(1)} = \sigma(i^{(1)}(h^{(1,K_1)}, x)) \odot (j^{(1)}(h^{(1,K_1)}))$$

$$\in \mathbb{R}^{(N \times f_1)}$$

Stage S:

$$h_i^{(S,1)} = GRU\left(h_i^{(S-1)}, \sum_e \sum_{j \in N^{(e)}(v_i)}^{N_{et}^{(S)}} NN^{(S,e)}\left(h_j^{(S-1)}, R_{ij}\right)\right) \quad (18)$$

$$\vdots$$

$$h_i^{(S,K_S)} = GRU\left(h_i^{(S,K_S-1)}, \sum_e \sum_{j \in N^{(e)}(v_i)}^{N_{et}^{(S)}} NN^{(S,e)}\left(h_j^{(S,K_S-1)}, R_{ij}\right)\right)$$

$$h^{(spatial)} = \sigma(i^{(S)}(h^{(S,K_S)}, h^{(S-1)})) \odot (j^{(S)}(h^{(S,K_S)}))$$

$$\in \mathbb{R}^{(N \times f_S)}$$

Map Atom Feature Maps to Parameters $q_i$=ChargeNN($h_i^{(spatial)}$)

$[l_{ij}, k_{b_{ij}}]$=BondNN($h_i^{(spatial)}, h_j^{(spatial)}$)

$[\theta_{ijk}, k_{aijk}]$=AngleNN($h_i^{(spatial)}, h_j^{(spatial)}, h_k^{(spatial)}$)

$[n_{ijkl}, \omega_{ijkl}, \gamma_{ijkl}]$=DihedralNN($h_i^{(spatial)}, h_j^{(spatial)}, h_k^{(spatial)}, h_l^{(spatial)}$) (19)

where $q_i$=ChargeNN($h_i^{(spatial)}$) is a neural network that maps each row vector of atom-level features to single scalars representing point charges. $[L_i, k_i]$=BondNN($h_i^{(spatial)}, h_j^{(spatial)}$) is a neural network that maps concatenated 2-tuples of atom-level features to equilibrium bond lengths and force constants, $[\theta_i, \chi_i]$=AngleNN($h_i^{(spatial)}, h_j^{(spatial)}, h_k^{(spatial)}$) is a neural network that maps concatenated 3-tuples of atom-level features to equilibrium angles and force constants, a neural network that maps concatenated 4-tuples of atom level features to equilibrium dihedral angles, frequencies and/or amplitudes, and a neural network mapping concatenated 2-tuples of atom level features to the van Der Waals force. In essence, each parameter in the new AMBER-like force field can be learned with neural networks based on atom features learned in the intermediate layers (or equivalently, the last layer) of the spatial graph convolutions. In a variety of embodiments, discrete edge types can be used with the spatial graph convolutions.

For new molecules not in the training set, processes in accordance with several embodiments of the invention can, in a single forward pass, input a fixed featurization x,A and output the point charges and other parameters necessary to conduct MD simulation in a molecular dynamics simulation package, such as (but not limited to) OpenMM, AMBER, DESMOND, and GROMACS. An additional computational step could be automated generation of a force field file, which is a relatively straightforward exercise.

Fully Graph Convolutional Potential

In many embodiments, systems and methods utilize an entirely new potential energy functional form trained end-to-end as a deep neural network predicated on a graph convolutional architecture. In the graph theory literature, "node-level outputs", which denote per-node scalars or vectors, are distinguished from a "graph-level output," which is a single scalar or vector that is a function of all nodes and edges in the graph. In some embodiments, graph-level output can be achieved through a "graph-gather" layer which is invariant to atom/node ordering:

$$h_i^{(1,1)} = GRU\left(x_i, \sum_e \sum_{j \in N^{(e)}(v_i)}^{N_{et}^{(1)}} NN^{(1,e)}(x_j, R_{ij})\right) \quad (20)$$

$$\vdots$$

$$h_i^{(1,K_1)} = GRU\left(h_i^{(1,K_1-1)}, \sum_e \sum_{j \in N^{(e)}(v_i)}^{N_{et}^{(1)}} NN^{(1,e)}\left(h_j^{(1,K_1-1)}, R_{ij}\right)\right)$$

$$h^{(1)} = \sigma(i^{(1)}(h^{(1,K_1)}, x)) \odot (j^{(1)}(h^{(1,K_1)}))$$

$$\in \mathbb{R}^{(N \times f_1)}$$

$$h_i^{(S,1)} = GRU\left(h_i^{(S-1)}, \sum_e \sum_{j \in N^{(e)}(v_i)}^{N_{et}^{(S)}} NN^{(S,e)}\left(h_j^{(S-1)}, R_{ij}\right)\right)$$

$$\vdots$$

$$h_i^{(S,K_S)} = GRU\left(h_i^{(S,K_S-1)}, \sum_e \sum_{j \in N^{(e)}(v_i)}^{N_{et}^{(S)}} NN^{(S,e)}\left(h_j^{(S,K_S-1)}, R_{ij}\right)\right)$$

$$h^{(spatial)} = \sigma(i^{(S)}(h^{(S,K_S)}, h^{(S-1)})) \odot (j^{(S)}(h^{(S,K_S)}))$$

$$\in \mathbb{R}^{(N \times f_S)}$$

$$h^{(FC_0)} = \sum_{j=1}^{N_{Lig}} h_j^{(S)}$$

$$h^{(FC_1)} = ReLU(W^{(FC_1)} h^{(FC_0)})$$

$$\vdots$$

$$h^{(FC_K)} = W^{(FC_K)} h^{(FC_{K-1})},$$

where the final weight matrix $W^{(FC_K)}$ has the same number of rows as the desired dimensionality of the final output $h^{(output)}$.

If the final output is a scalar value, and a spatial graph convolution model (or PotentialNet) is trained with input molecular systems connected to energy values as a label, models in accordance with some embodiments of the invention can be treated as a potential energy function:

$$\phi(x,A,R) = \text{PotentialNet}(x,A,R) \quad (21)$$

Computation of the potential energy $\phi(x,A,R)$ in accordance with several embodiments of the invention requires, for each graph convolutional layer $\mathcal{O}(N_{neighbors} \cdot N \cdot N_{parameters})$ calculations. Without neighbor listing, a technique used in the molecular simulation community, this computational cost can climb to $\mathcal{O}(N^2 \cdot N_{parameters})$. For each of the N atoms, one must compute either $N_{neighbors}$ in the former case or N−1 in the latter case feed forward neural networks to obtain the overall message per graph convolutional layer.

The AMBER force field functional form has successfully enabled the elucidation of biomacromolecular and small molecule dynamics, as well as the interaction between them. In some embodiments, the computation of the total potential energy is calculated as the sum of the AMBER functional form (with either fixed or learnable parameters with GAFF as an initial guess) with spatial graph convolutions (or PotentialNet):

$$\phi(x,A,R) = \text{PotentialNet}(x,A,R) + \text{AMBER}(\text{bonds,angles, torsions}) \quad (22)$$

In some embodiments, a combination of the AMBER functional form and the spatial graph convolutions (or AmberNet) is envisioned:

$$\phi(x,A,R) = \text{PotentialNet}(x,A,R) + \text{AmberNet}(x,A,R) \quad (23)$$

In a number of embodiments, the total number of network parameters in such a hybrid can be reduced by sharing the intermediate layers that derive the atom features $h^{(spatial)}$.

Featurizing each conformation of a molecule can entail (a) atom-level features, which could be as simple as one-hot features of each element and its hybridization type, (b) adjacency tensor of bonds, and (c) interatomic distances. In a number of embodiments, a neural network regressor is trained based on PotentialNet to map the input x, A, and R of each conformer to an energy. Cross validation strategies in accordance with several embodiments of the invention include, but are not limited to, random, temporal (if available), scaffold, and SMILES distance agglomerative splitting. The aim here should be to achieve state-of-the-art energy estimates on par with experimental or DFT error.

In some embodiments, after training PotentialNet(x, A, R) (e.g., with the ANI-1 and/or other datasets that map conformers to energy values), the parameters of such a model can be fixed to yield $\hat{\phi}(x,A,R)$.

In a Newtonian system, one can write the force on the atoms:

$$F = -\nabla_{(r_1, r_2, \ldots, r_N)} \hat{\phi}(x,A,R) \quad (24)$$

In certain embodiments, the gradient $\nabla_{(r_1, r_2, \ldots, r_N)} \hat{\phi}(x,A,R)$ can be computed with the backpropagation algorithm, implemented by numerous deep neural network software packages. Given input features x, input adjacency matrix A, and initial positions $R_0$, an initial estimate of the energy $\hat{\phi}(x,A,R_0)$ can be obtained with a single forward pass of the network. Backpropagation would then yield first derivative information on the coordinates encoded in R. Subsequently, the gradient information encoded in $\nabla\hat{\phi}$ can be used, in accordance with some embodiments of the invention, to move the positions of the N atoms so as to reduce the energy $\hat{\phi}$. While an interatomic distance matrix R could be input as a feature, in a number of embodiments, the initial three-dimensional positions x,y,z can serve as input features and R can then be easily be computed differentiably within the neural network. The gradient in accordance with many embodiments of the invention can be used with some small step size to update the x,y,z positions of each atom. Subsequently, in some embodiments, the gradient can be re-computed with the updated coordinates and resultant distance matrix $R_1$, $\nabla_{(r_1, r_2, \ldots, r_N)} \hat{\phi}(x,A,R_1)$, the positions can be updated again, and the process can iteratively continue until the computed forces $\nabla_{(r_1, r_2, \ldots, r_N)} \hat{\phi}(x,A,R)$ fall below a certain tolerance.

In a Newtonian system, one can write the equations of motion as:

$$a = \frac{F}{m} = \frac{-\nabla_{(r_1, r_2, \ldots, r_N)} \hat{\phi}(x, A, R)}{m} \quad (25)$$

Processes in accordance with many embodiments of the invention can propagate the positions of the atoms given some initial coordinates (and associated interatomic distance matrix $R_0$) using a variety of methods, including (but not limited to) the velocity Verlet algorithm. Initial velocities can be determined by a statistical mechanical technique such as (but not limited to) the Maxwell-Boltzmann distribution, whereas initial positions can be determined through a combination of crystallography and energy minimization. Energy minimization in accordance with several embodiments of the invention can be conducted with methods such as those described above. In certain embodiments, a training dataset does not contain water molecules in different conformers and it therefore can be desirable to add a TIP3P or similar potential to $\hat{\phi}(x,A,R)$ in (25).

In numerous embodiments, it can be desirable to conduct the first MD simulations with a GCP solely in dihedral space. It has been argued by some biophysicists that much of the biologically relevant dynamics of macromolecules stem solely from dihedral motions of rotatable bonds. A dihedral, or torsion angle, is defined by the angle between the two planes defined by a contiguous series of four bonded atoms. There are multiple ways to constrain a molecular simulation to dihedral space. First, in some embodiments, the gradient of the potential can be taken directly with respect to the d dihedral angles θ:

$$\frac{-\nabla_{(\theta_1, \theta_2, \ldots, \theta_d)} \hat{\phi}(x, A, R)}{m} \quad (26)$$

In turn, processes in accordance with some embodiments of the invention can compute further derivatives to propagate the dihedral/internal coordinate space derivatives to derivatives in terms of the raw x,y,z coordinates. One skilled in the art will recognize that there are numerous methods for performing MD in dihedral space.

In various embodiments, either the fully graph convolutional energy from PotentialNet or alternatively AmberNet can be used as the basis for a molecular docking energy function. In numerous embodiments, by seeding a given conformation of a given ligand in a certain orientation, either energy minimization or stochastic dynamic simulation can be used to predict a global energy minimum conformation, or docked pose, of the ligand in a receptor. As described above, different variants of PotentialNet can be used to predict the binding free energy/binding affinity/potency of a given ligand-protein interaction. In some embodiments, processes can combine the purely graph convolutional form of PotentialNet with an AmberNet like potential. By computing a binding energy as $$\Delta G(x,A,R) = \text{PotentialNet}(x,A,R) + \text{AmberNet}(x,A,R) \quad (27)$$

one could incorporate such concepts as conformational entropy, torsional strain terms, intramolecular clashes, and other concepts from classical molecular docking approaches but derive those parameters with deep neural networks. In numerous embodiments, graph convolutions can be a natural functional form for computing a reaction coordinate to monitor and drive collective dynamics of a biomolecular system.

Although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A method performed by one or more computers for training a graph neural network having a plurality of weights to perform molecular property prediction, the method comprising:
    obtaining spatial distance data for a plurality of molecules, wherein the plurality of molecules comprise a plurality of atoms, wherein the spatial distance data defines, for each pair of atoms from the plurality of molecules, a respective three-dimensional (3D) spatial distance between the pair of atoms in a 3D spatial configuration of the atoms in the plurality of molecules;
    generating data defining a graph representing the plurality of molecules based at least in part on the spatial distance data defining 3D spatial distances between pairs of atoms from the plurality of molecules, wherein:
        the graph representing the plurality of molecules comprises a set of nodes and a set of edges, and each node in the graph represents a respective atom from the plurality of molecules;
        generating the data defining the graph comprises:
        determining, for each pair of nodes in the graph, whether the pair of nodes should be connected by an edge based at least in part on a 3D spatial distance between a corresponding pair of atoms in the 3D spatial configuration of the atoms in the plurality of molecules; and
        generating, for each pair of nodes in the graph that should be connected by an edge, a respective edge that connects the pair of nodes in the graph; and
        the set of edges of the graph comprises a plurality of inter-molecule edges, wherein each inter- molecule edge connects a respective pair of nodes representing a pair of atoms comprising a first atom in a first molecule and a second atom in a second, different molecule;
            performing a set of graph convolutions, by a graph neural network and in accordance with a plurality of weights of the graph neural network, on a second the graph representing the plurality of molecules;
    processing, by the graph neural network and in accordance with the plurality of weights of the graph neural network, a result of the set of graph convolutions to generate a set of one or more characteristics for the plurality of molecules;
    determining gradients of a loss function that measures an error in the prediction, generated by the graph neural network, of the set of one or more characteristics for the plurality of molecules; and
    updating the plurality of weights of the graph neural network using the gradients of the loss function.

2. The method of claim 1, wherein the plurality of molecules comprises at least a ligand molecule and a target molecule.

3. The method of claim 1, wherein the set of one or more characteristics for the plurality of molecules comprises one or more of: a toxicity of the plurality of molecules, a solubility of the plurality of molecules, a binding affinity of the plurality of molecules, or quantum properties of the plurality of molecules.

4. The method of claim 1, further comprising providing data defining the set of one or more characteristics for the set of plurality of molecules for use in performing drug discovery.

5. The method of claim 1, wherein the loss function measures the error in the prediction using a cross-entropy loss.

6. A system comprising:
    a non-transitory memory communicatively coupled to the one or more computers, wherein the non-transitory memory stores instructions that, when executed by the one or more computers, cause the one or more computers to perform operations for training a graph neural network having a plurality of weights to perform molecular property prediction, the operations comprising:
        obtaining spatial distance data for a plurality of molecules, wherein the plurality of molecules comprises a plurality of atoms, wherein the spatial distance data defines, for each pair of atoms from the plurality of molecules, a respective three-dimensional (3D) spatial distance between the pair of atoms in a 3D spatial configuration of the atoms in the plurality of molecules;
    generating data defining a graph representing the plurality of molecules based at least in part on the spatial distance data defining 3D spatial distances between pairs of atoms from the plurality of molecules, wherein:
        the graph representing the plurality of molecules comprises a set of nodes and a set of edges, and each node in the graph represents a respective atom from the plurality of molecules;
        generating the data defining the graph comprises:
        determining, for each pair of nodes in the graph, whether the pair of nodes should be connected by an edge based at least in part on a 3D spatial distance between a corresponding pair of atoms in the 3D spatial configuration of the atoms in the plurality of molecules; and
        generating, for each pair of nodes in the graph that should be connected by an edge, a respective edge that connects the pair of nodes in the graph; and
        the set of edges of the graph comprises a plurality of inter-molecule edges, wherein each inter-molecule edge connects a respective pair of nodes representing a pair of atoms comprising a first atom in a first molecule and a second atom in a second, different molecule;
        performing a set of graph convolutions, by the a graph neural network and in accordance with a plurality of weights of the graph neural network, on the graph representing the plurality of molecules;
    processing, by the graph neural network and in accordance with the plurality of weights of the graph neural network, a result of the set of graph convolutions to generate predicting a set of one or more characteristics for the plurality of molecules;
        determining gradients of a loss function that measures an error in the prediction, generated by the graph neural network, of the set of one or more characteristics for the plurality of molecules; and
        updating the plurality of weights of the graph neural network using the gradients of the loss function.

7. A non-transitory memory storing instructions that when executed by one or more computers cause the one or more computers to perform operations for training a graph neural network having a plurality of weights to perform molecular property prediction, the operations comprising:

obtaining spatial distance data for a plurality of molecules, wherein the plurality of molecules comprise a plurality of atoms, wherein the spatial distance data defines, for each pair of atoms from the plurality of molecules, a respective three-dimensional (3D) spatial distance between the pair of atoms in a 3D spatial configuration of the atoms in the plurality of molecules;

generating data defining a graph representing the plurality of molecules based at least in part on the spatial distance data defining 3D spatial distances between pairs of atoms from the plurality of molecules, wherein:

the graph representing the plurality of molecules comprises a set of nodes and a set of edges, and each node in the graph represents a respective atom from the plurality of molecules;

generating the data defining the graph comprises:

determining, for each pair of nodes in the graph, whether the pair of nodes should be connected by an edge based at least in part on a 3D spatial distance between a corresponding pair of atoms in the 3D spatial configuration of the atoms in the plurality of molecules; and generating, for each pair of nodes in the graph that should be connected by an edge, a respective edge that connects the pair of nodes in the graph; and the set of edges of the graph comprises a plurality of inter-molecule edges, wherein each inter-molecule edge connects a respective pair of nodes representing a pair of atoms comprising a first atom in a first molecule and a second atom in a second, different molecule;

performing a set of graph convolutions, by a graph neural network and in accordance with a plurality of weights of the graph neural network, on the graph representing the plurality of molecules;

processing, by the graph neural network and in accordance with the plurality of weights of the graph neural network, a result of the set of graph convolutions to generate a set of one or more characteristics for the plurality of molecules;

determining gradients of a loss function that measures an error in the prediction, generated by the graph neural network, of the set of one or more characteristics for the plurality of molecules; and updating the plurality of weights of the graph neural network using the gradients of the loss function.

8. The non-transitory memory of claim 7, wherein the set of one or more characteristics for the plurality of molecules comprises one or more of: a toxicity of the plurality of molecules, a solubility of the plurality of molecules, a binding affinity of the plurality of molecules, or quantum properties of the plurality of molecules.

9. The non-transitory memory of claim 7, wherein the operations further comprise:

providing data defining the set of one or more characteristics for the plurality of molecules for use in performing drug discovery.

10. The non-transitory memory of claim 7, wherein the loss function measures the error in the prediction using a cross-entropy loss.

11. he method of claim 1, wherein for one or more pairs of nodes in the graph, determining whether the pair of nodes should be connected by an edge comprises:

determining whether the pair of nodes should be connected by an edge based on whether a 3D spatial distance between the corresponding pair of atoms satisfies a threshold.

12. he method of claim 11, wherein for one or more pairs of nodes in the graph, determining whether the pair of nodes should be connected by an edge based on whether the 3D spatial distance between the corresponding pair of atoms satisfies a threshold comprises:

determining that the pair of nodes should be connected by an edge based on the 3D spatial distance between the corresponding pair of atoms being less than the threshold.

13. he method of claim 11, wherein for one or more pairs of nodes in the graph, determining whether the pair of nodes should be connected by an edge based on whether the 3D spatial distance between the corresponding pair of atoms satisfies a threshold comprises:

determining that the pair of nodes should not connected by an edge based on the 3D spatial distance between the corresponding pair of atoms being greater than the threshold.

14. he method of claim 1, further comprising:

generating data defining one or more second graphs representing the plurality of molecules based at least in part on bond data defining bonds between pairs of atoms from the plurality of molecules; and performing a second set of graph convolutions, by the graph neural network and in accordance with the plurality of weights of the graph neural network, on the one or more second graphs representing the plurality of molecules.

15. he method of claim 14, wherein generating the set of one or more characteristics for the plurality of molecules further comprises:

processing, by the graph neural network and in accordance with the plurality of weights of the graph neural network, a result of the second set of graph convolutions.

16. The method of claim 1, wherein the set of edges of the graph comprises a plurality of intra-molecule edges, wherein each intra-molecule edge connects a respective pair of nodes representing a pair of atoms comprising a first atom and a second atom in a same molecule.

17. The method of claim 1, wherein processing, by the graph neural network and in accordance with the plurality of weights of the graph neural network, a result of the set of graph convolutions to generate a set of one or more characteristics for the plurality of molecules comprises:

performing a graph gather operation to produce a feature vector; and processing the feature vector to generate the set of one or more characteristics for the plurality of molecules.

18. The method of claim 17, wherein performing the graph gather operation to produce the feature vector comprises:

identifying a molecule from the plurality of molecules as a ligand molecule; and performing the graph gather operation solely over embeddings representing atoms included in the ligand molecule.

19. The system of claim 6, wherein for one or more pairs of nodes in the graph, determining whether the pair of nodes should be connected by an edge comprises:

determining whether the pair of nodes should be connected by an edge based on whether a 3D spatial distance between the corresponding pair of atoms satisfies a threshold.

20. The system of claim 19, wherein for one or more pairs of nodes in the graph, determining whether the pair of nodes should be connected by an edge based on whether the 3D spatial distance between the corresponding pair of atoms satisfies a threshold comprises:
  determining that the pair of nodes should be connected by an edge based on the 3D spatial distance between the corresponding pair of atoms being less than the threshold.

\* \* \* \* \*

UNITED STATES PATENT AND TRADEMARK OFFICE
CERTIFICATE OF CORRECTION

PATENT NO. : 11,727,282 B2
APPLICATION NO. : 16/293586
DATED : August 15, 2023
INVENTOR(S) : Evan Nathaniel Feinberg, Vijay Satyanand Pande and Bharath Ramsundar It is certified that error appears in the above-identified patent and that said Letters Patent is hereby corrected as shown below:

In the Claims

Column 33, Line 61, Claim 11, "he method of claim 1" should be changed to --The method of claim 1--;
Column 34, Line 1, Claim 12, "he method of claim 11" should be changed to --The method of claim 11--; Line 10, Claim 13, "he method of claim 11" should be changed to --The method of claim 11--; Line 19, Claim 14, "he method of claim 1" should be changed to --The method of claim 1--; Line 29, Claim 15, "he method of claim 1" should be changed to --The method of claim 1--.

Signed and Sealed this
Twenty-seventh Day of February, 2024

Katherine Kelly Vidal
*Director of the United States Patent and Trademark Office*